United States Patent
Kozlov et al.

(10) Patent No.: US 9,574,944 B1
(45) Date of Patent: Feb. 21, 2017

(54) SYSTEMS AND METHODS FOR HIGH-CONTRAST, NEAR-REAL-TIME ACQUISITION OF TERAHERTZ IMAGES

(71) Applicant: Microtech Instruments, Inc., Eugene, OR (US)

(72) Inventors: Vladimir G. Kozlov, Eugene, OR (US); Patrick F. Tekavec, Eugene, OR (US)

(73) Assignee: MICROTECH INSTRUMENTS, INC., Eugene, OR (US)

( * ) Notice: Subject to any disclaimer, the term of this patent is extended or adjusted under 35 U.S.C. 154(b) by 0 days.

(21) Appl. No.: 15/173,504

(22) Filed: Jun. 3, 2016

Related U.S. Application Data

(63) Continuation-in-part of application No. 14/561,141, filed on Dec. 4, 2014, now Pat. No. 9,377,362.

(60) Provisional application No. 61/912,004, filed on Dec. 4, 2013, provisional application No. 62/007,904, filed on Jun. 4, 2014.

(51) Int. Cl.
*G01J 5/08* (2006.01)

(52) U.S. Cl.
CPC .......... *G01J 5/0803* (2013.01); *G01J 5/0806* (2013.01)

(58) Field of Classification Search
CPC .............................. G01J 5/0803; G01J 5/0806
See application file for complete search history.

(56) References Cited

U.S. PATENT DOCUMENTS

| | | | |
|---|---|---|---|
| 4,897,562 A | 1/1990 | Krasinski et al. | |
| 5,623,145 A | 4/1997 | Nuss | |
| 5,710,430 A | 1/1998 | Nuss | |
| 5,789,750 A | 8/1998 | Nuss | |
| 5,894,125 A | 4/1999 | Brener et al. | |
| 5,939,721 A | 8/1999 | Jacobsen et al. | |
| 5,952,771 A | 9/1999 | Zhang et al. | |
| 6,078,047 A | 6/2000 | Mittleman et al. | |
| 6,151,155 A | 11/2000 | Durfee et al. | |
| 6,414,473 B1 | 7/2002 | Zhang et al. | |
| 7,272,158 B1 | 9/2007 | Hayes et al. | |
| 7,339,718 B1 | 3/2008 | Vodopyanov et al. | |
| 7,349,609 B1 | 3/2008 | Vodopyanov et al. | |
| 7,929,580 B2 | 4/2011 | Moeller | |
| 8,035,083 B1 | 10/2011 | Kozlov et al. | |

(Continued)

FOREIGN PATENT DOCUMENTS

WO    WO 03/042670    5/2003

OTHER PUBLICATIONS

Schaar et al; "Intracavity Terahertz Generation in a Synchronously Pumped Optical Parametric Oscillator using Quasiphasematched GaAs"; Conference on Lasers and Electro-Optics, Paper No. CThl6 (2007).

(Continued)

*Primary Examiner* — David Porta
*Assistant Examiner* — Faye Boosalis
(74) *Attorney, Agent, or Firm* — David S. Alavi

(57) ABSTRACT

A cw terahertz image beam is upconverted by a nonlinear optical process (e.g., sum- or difference-frequency generation with a near IR cw upconverting beam). The upconverted image is acquired by a near IR image detector. The bandwidths and center wavelengths of the terahertz image beam and the upconverting beam are such that wavelength filtering can be employed to permit an upconverted image beam to reach the detector while blocking or substantially attenuating the upconverting beam.

34 Claims, 17 Drawing Sheets

(56) References Cited

U.S. PATENT DOCUMENTS

| | | |
|---|---|---|
| 8,514,393 B2 | 8/2013 | Khan et al. |
| 8,599,474 B1 | 12/2013 | Kozlov et al. |
| 8,599,475 B1 | 12/2013 | Kozlov et al. |
| 8,599,476 B1 | 12/2013 | Kozlov et al. |
| 2012/0194901 A1 | 8/2012 | Bravo-Abad et al. |
| 2015/0153234 A1 | 6/2015 | Kozlov et al. |

OTHER PUBLICATIONS

Schaar et al; Terahertz Sources Based on Intracavity Parametric Down-Conversion in Quasi-Phase-Matched Gallium Arsenide; IEEE J Sel Topics Quant Electron vol. 14 No. 2 p. 354 (2008).

Jiang et al; "Improvement of terahertz imaging with a dynamic subtraction technique"; Applied Optics vol. 39 No. 17 p. 2982 (2000).

Nahata et al; "Two-dimensional imaging of continuous-wave terahertz radiation using electro-optic detection"; Applied Physics Letters vol. 81 No. 6 p. 963 (2002).

Yonera et al; "Millisecond THz imaging based on two-dimensional EO sampling using a high speed CMOS camera"; Conference on Lasers and Electro-Optics, Paper No. CMB3 (2004).

Ding et al; "Phase-Matched THz Frequency Upconversion in a GaP Crystal"; Conference on Lasers and Electro-Optics, Paper No. CTuL3 (2006).

Ding et al; "Observation of THz to near-Infrared parametric conversion in ZnGeF2 crystal"; Optics Express vol. 14 No. 18 p. 8311 (2006).

Hurlbut et al: "THz-wave generation inside a high-finesse ring-cavity OPO pumped by a fiber laser"; vol. 7582 p. 75820Z-1 (2010).

Cao et al; "Coherent detection of pulsed narrowband terahertz radiation"; Applied Physics Letters vol. 88 p. 011101 (2006).

Vodopyanov; "Optical generation of narrow-band terahertz packets in periodically inverted electro-optic crystals . . . "; Optics Express vol. 14 No. 6 p. 2263 (2006).

Lee et al; "Generation of multicycle terahertz pulses via optical rectification in periodically inverted GaAs structures"; Applied Physics Letters vol. 89 p. 181104 (2006).

Khan et al; "Optical detection of terahertz radiation by using nonlinear parametric upconversion"; Optics Letters vol. 32 No. 22 p. 3248 (2007).

Schaar et al; "Intracavity terahertz-wave generation in a synchronously pumped optical parametric oscillator . . . "; Optics Letters vol. 32 No. 10 p. 1284 (2007).

Khan et al; "Optical detection of terahertz using nonlinear parametric upconversion"; Optics Letters vol. 33 No. 23 p. 2725 (2008).

Vodopyanov at al; "Resonantly-enhanced THz-wave generation via multispectral mixing . . . "; Conference on Lasers and Electro-Optics, Paper No. CTuG1 (2009).

Pedersen et al; "Enhanced 2D image upconve sion using solid-state lasers"; Optics Express vol. 17 No. 23 p. 20885 (2009).

Hurlbut et al; "THz-wave generation inside a high-finesse ring-cavity OPO pumped by a fiber laser"; Conference on Lasers and Electro-Optics, Paper No. CWF3 (2010).

Tekavec et al; "Efficient high-power tunable terahertz sources based on intracavity difference frequency generation"; Paper No. IRMMW THz in 36th Int'l Conf on Infrared, Millimeter and Terahertz Waves (2011).

Tekavec et al; "Terahertz generation from quasi-phase matched gallium arsenide using a type II ring cavity optical parametric oscillator"; Proc. SPIE 8261, Terahertz Technology and Applications V, 82610V; doi: 10.1117/12.909529 (2012).

Clerici et al; "CCD-based imaging and 3D space-time mapping of terahertz fields via Kerr frequency conversion"; Optics Letters vol. 38 No. 11 p. 1899 (Jun. 1, 2013).

Fan et al; "Room temperature terahertz wave imaging at 60 fps by frequency up-conversion in DAST crystal"; Proc. SPIE 8964, Nonlinear Frequency Generation and Conversion: Materials, Devices, and Applications XIII, 89640F3 (Feb. 20, 2014); doi:10.1117/12.2038685.

Tekavec et al, Video Rate THz imaging based on frequency upconversion using a near-IR CMOS camera: CLEO: Science and Innovations 2014 (San Jose, California United States Jun. 8-13, 2014; ISBN: 978-1-55752-999-2.

International Search Report dated Sep. 18, 2015 in counterpart App No. PCT/US2014/068662.

Ghotbi et al; "990 mW average power, 52% efficient, high-repetition-rate picosecond-pulse generation in the blue with BiB3O6"; Optics Letters, vol. 30. No. 24 p. 3395; Dec. 15, 2005.

Zhang et al, "Terahertz imaging via Eiectrooptic Effect"; IEEE Trans Microwave Theory & Tech vol. 47 No. 12 p. 2644 (1999).

Vodopyanov et al; "Terahertz-wave generation in quasi-phase atched GaAs"; App Phys Lett vol. 89 p. 141119 (2006).

Vodopyanov et al; "Terahertz-wave generation in quasi-.phase-matched GaAs"; App Phys Lett vol. 89 p. 141119 (2006); equivalent to Conference on Lasers and Electro-Optics, Paper No. CTuGG (2006).

Fan et al; "Real-time terahertz wave imaging by nonlinear optical frequency up-conversion in a 4-dimethylamino-N'-methyl-4-stilbazolium tosylate crystal"; Applied Physics Letters, 104, 101106 (2014); doi:10.1063/1.4668134.

Tekavec et al; "Video Rate 3D THz tomography": rejected post-deadline paper, Conference on Lasers and Electro-optics (Jun. 8-13, 2014, San Jose, California).

Wu et al; "Two-dimensional electro-optic imaging of THz beams"; Applied Physics Letters vol. 69 No. 8 p. 1026 (1996).

Jiang et al; "Terahertz imaging via electrooptic effect"; IEEE Transactions on Microwave Theory and Techniques vol. 47 No. 12 p. 2644 (1999).

Hurlbut et al: "THz wave generation inside a high-finesse ring-cavity OPO pumped by a fiber laser"; Proc SPIE vol. 7582 p. 75820Z-1 (2010).

| THz detection technology | fs electro-optic detection[a] | cw THz + ns upconverting[b] | cw THz + ps upconverting[c] | ps THz + ps upconverting[c] | cw THz + cw upconverting[d] |
|---|---|---|---|---|---|
| $v_{THz}$; $\lambda_{UC}$ | 1.5 THz; 800 nm | 0.7 THz; 1550 nm | | 1.55 THz; 1064 nm | 0.7 THz; 1.5 μm |
| Pulse duration (THz) | 1 ps | cw | | 6 ps | cw |
| Pulse Duration (IR) | 250 fs | 10 ns | | 6ps | cw |
| THz Power (Peak, Avg.) | 360 mW, 10 μW | 2.5 mW, 2.5 mW | | 450 mW, 300 μW | 1 W, 1 W |
| IR Power (Peak, Avg.) | 11 W, 300 μW | 50 W, 100 mW | | 150 W, 100 mW | 15 W, 15 W |
| Sample[e] (# of QPM wafers) | 4 mm ZnTe | 4 mm GaAs (N=1) | | 3.74 mm GaAs (N=12) | 5 mm GaAs (N=1) |
| Efficiency of Upconversion[f] | $5.5\times10^{-5}$ | $1.45\times10^{-4}$ | | 0.001 | $\sim 10^{-5}$ |
| Calculated Avg. signal power | 0.55 nW | 0.73 nW | | 300 nW | $\sim$ 10 μW |
| FOM[g] | 0.18(h) | $7.3\times10^{-2}$ (i) | | $3\times10^4$ (j) | $\sim 10^4$ (j) | a) Parameters taken from Wu et al
b) Parameters taken from Khan et al; Optics Letters
c) Parameters taken from Kozlov et al; US 2015/0153234
d) Parameters for inventive system of instant disclosure
e) For ZnTe, the QPM period is longer than the crystal used. For GaAs, the coherence length is ~4mm for 1550 nm pump and 0.312 mm for 1064 nm pump f) $\eta_{SFG} = \dfrac{8\pi^2\left(\frac{2}{\pi}\right)^2 d_{eff}^2 (NL_C)^2 I_{pump}}{\epsilon_0 n_{THz} n_{pump} n_{sum} c \lambda_{sum}^2}$ g) FOM defined as the as the ratio of the detected power to the attenuated probe power.
h) Assuming a polarizer with $10^5$:1 extinction ratio is used to attenuate the probe
i) Assuming spectral filtering of the pump with 70 dB attenuation
j) Assuming total attenuation of $10^{10}$

FIG. 4

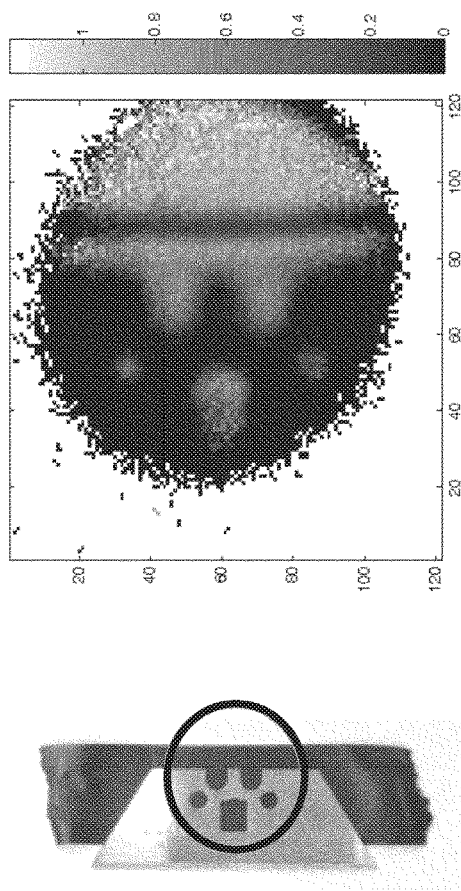
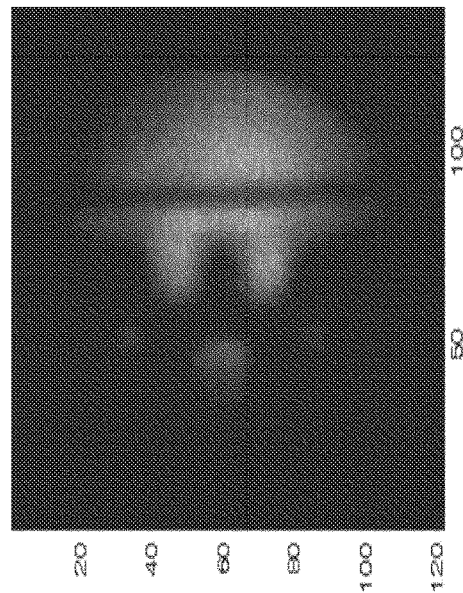
FIG. 9A
FIG. 10A
FIG. 11A

SYSTEMS AND METHODS FOR HIGH-CONTRAST, NEAR-REAL-TIME ACQUISITION OF TERAHERTZ IMAGES

This application is a continuation-in-part of U.S. non-provisional application Ser. No. 14/561,141 filed Dec. 4, 2014 in the names of Vladimir G. Kozlov and Patrick F. Tekavec (now U.S. Pat. No. 9,377,362), which in turn claims benefit of (i) U.S. provisional App. No. 61/912,004 filed Dec. 4, 2013 in the names of Vladimir G. Kozlov and Patrick F. Tekavec, and (ii) U.S. provisional App. No. 62/007,904 filed Jun. 4, 2014 in the names of Vladimir G. Kozlov and Patrick F. Tekavec. Each one of said applications is hereby incorporated by reference as if fully set forth herein.

FIELD OF THE INVENTION

The field of the present invention relates to imaging using terahertz-frequency radiation. In particular, systems and methods are disclosed for high-contrast, near-real-time acquisition of terahertz images.

BACKGROUND

A number of systems and methods for generation, detection, or imaging with terahertz-frequency radiation have been disclosed previously. Some of those are disclosed in:

U.S. Pat. No. 5,623,145 entitled "Method and apparatus for terahertz imaging" issued Apr. 22, 1997 to Nuss (Lucent Technologies Inc.);

U.S. Pat. No. 5,710,430 entitled "Method and apparatus for terahertz imaging" issued Jan. 20, 1998 to Nuss (Lucent Technologies Inc.);

U.S. Pat. No. 5,789,750 entitled "Optical system employing terahertz radiation" issued Aug. 4, 1998 to Nuss (Lucent Technologies Inc.);

U.S. Pat. No. 5,894,125 entitled "Near field terahertz imaging" issued Aug. 18, 1997 to Brener et al (Lucent Technologies Inc.);

U.S. Pat. No. 5,939,721 entitled "Systems and methods for processing and analyzing terahertz waveforms" issued Aug. 17, 1999 to Jacobsen et al (Lucent Technologies Inc.);

U.S. Pat. No. 5,952,721 entitled "Electro-optical sensing apparatus and method for characterizing free-space electromagnetic radiation" issued Sep. 14, 1999 to Zhang et al (Rensselaer Polytechnic Institute);

U.S. Pat. No. 6,078,047 entitled "Method and apparatus for terahertz tomographic imaging" issued Jun. 20, 2000 to Mittleman et al (Lucent Technologies Inc.);

U.S. Pat. No. 6,414,473 entitled "electro-optic/magneto-optic measurement of electromagnetic radiation using chirped optical pulse" issued Jul. 2, 2002 to Zhang et al (Rensselaer Polytechnic Institute);

Pub. No. WO 2003/042670 entitled "Method and system for performing three-dimensional terahertz imaging on an object" published May 22, 2003 in the names of Ferguson et al (Rensselaer Polytechnic Institute);

U.S. Pat. No. 7,272,158 entitled "Highly efficient waveguide pulsed THz electromagnetic radiation source and group-matched waveguide THz electromagnetic radiation source" issued Sep. 18, 2007 to Hayes et al;

U.S. Pat. No. 7,339,718 entitled "Generation of terahertz radiation in orientation-patterned semiconductors" issued Mar. 4, 2008 to Vodopyanov et al (Microtech Instruments, Oregon State University, Stanford University);

U.S. Pat. No. 7,349,609 entitled "Terahertz radiation generation and methods therefor" issued Mar. 25, 2008 to Vodopyanov et al;

U.S. Pat. No. 7,929,580 entitled "Inexpensive Terahertz Pulse Wave Generator" issued Apr. 19, 2011 to Moeller (Alcatel-Lucent USA Inc.);

U.S. Pat. No. 8,035,083 entitled "Terahertz tunable sources, spectrometers, and imaging systems" issued Oct. 11, 2011 to Kozlov et al (Microtech Instruments Inc.);

U.S. Pub. No. 2012/0008140 entitled "Terahertz sensing system and method" published Jan. 12, 2012 in the names of Khan et al (Massachusetts Institute of Technology; now U.S. Pat. No. 8,514,393 issued Aug. 20, 2013);

U.S. Pat. No. 8,599,474 entitled "Alignment and optimization of a synchronously pumped optical parametric oscillator for nonlinear optical generation" issued Dec. 3, 2013 to Kozlov et al (Microtech Instruments);

U.S. Pat. No. 8,599,475 entitled "Alignment and optimization of a synchronously pumped optical parametric oscillator for nonlinear optical generation" issued Dec. 3, 2013 to Kozlov et al (Microtech Instruments);

U.S. Pat. No. 8,599,476 entitled "Alignment and optimization of a synchronously pumped optical parametric oscillator for nonlinear optical generation" issued Dec. 3, 2013 to Kozlov et al (Microtech Instruments);

Wu et al; "Two-dimensional electro-optic imaging of THz beams"; Applied Physics Letters Vol. 69 No. 8 p. 1026 (1996);

Jiang et al; "Terahertz imaging via electrooptic effect"; IEEE Transactions on Microwave Theory and Techniques Vol. 47 No. 12 p. 2644 (1999);

Jiang et al; "Improvement of terahertz imaging with a dynamic subtraction technique"; Applied Optics Vol. 39 No. 17 p. 2982 (2000);

Nahata et al; "Two-dimensional imaging of continuous-wave terahertz radiation using electro-optic detection"; Applied Physics Letters Vol. 81 No. 6 p. 963 (2002);

Sutherland et al; *Handbook of Nonlinear Optics* 2ed (2003); New York: Marcel Dekker;

Yonera et al; "Millisecond THz imaging based on two-dimensional EO sampling using a high speed CMOS camera"; Conference on Lasers and Electro-Optics, Paper No. CMB3 (2004);

Ding et al; "Phase-Matched THz Frequency Upconversion in a GaP Crystal"; Conference on Lasers and Electro-Optics, Paper No. CTuL3 (2006);

Ding et al; "Observation of THz to near-Infrared parametric conversion in ZnGeP2 crystal"; Optics Express Vol. 14 No. 18 p. 8311 (2006);

Hurlbut et al; "Quasi-Phasematched THz Generation in GaAs"; Conference on Lasers and Electro-Optics, Paper No. CTuGG (2006);

Cao et al; "Coherent detection of pulsed narrowband terahertz radiation"; Applied Physics Letters Vol. 88 p. 011101 (2006);

Vodopyanov; "Optical generation of narrow-band terahertz packets in periodically inverted electro-optic crystals: conversion efficiency and optimal laser pulse format"; Optics Express Vol. 14 No. 6 p. 2263 (2006);

Lee et al; "Generation of multicycle terahertz pulses via optical rectification in periodically inverted GaAs structures"; Applied Physics Letters Vol. 89 p. 181104 (2006);

Khan et al; "Optical detection of terahertz radiation by using nonlinear parametric upconversion"; Optics Letters Vol. 32 No. 22 p. 3248 (2007);

Schaar et al; "Intracavity terahertz-wave generation in a synchronously pumped optical parametric oscillator using quasi-phase-matched GaAs"; Optics Letters Vol. 32 No. 10 p. 1284 (2007);

Khan et al; "Optical detection of terahertz using nonlinear parametric upconversion"; Optics Letters Vol. 33 No. 23 p. 2725 (2008);

Vodopyanov et al; "Resonantly-enhanced THz-wave generation via multispectral mixing inside a ring-cavity optical parametric oscillator"; Conference on Lasers and Electro-Optics, Paper No. CTuG1 (2009);

Pedersen et al; "Enhanced 2D-image upconversion using solid-state lasers"; Optics Express Vol. 17 No. 23 p. 20885 (2009).

Hurlbut et al; "THz-wave generation inside a high-finesse ring-cavity OPO pumped by a fiber laser"; Conference on Lasers and Electro-Optics, Paper No. CWF3 (2010);

Tekavec et al; "Efficient high-power tunable terahertz sources based on intracavity difference frequency generation"; Paper No. IRMMW-THz in 36th International Conference on Infrared, Millimeter and Terahertz Waves (2011); and Tekavec et al; "Terahertz generation from quasi-phase matched gallium arsenide using a type II ring cavity optical parametric oscillator"; Proc. SPIE 8261, Terahertz Technology and Applications V, 82610V; doi:10.1117/12.909529 (2012);

Clerici et al; "CCD-based imaging and 3D space-time mapping of terahertz fields via Kerr frequency conversion"; Optics Letters Vol. 38 No. 11 p. 1899 (Jun. 1, 2013);

Fan et al; "Room temperature terahertz wave imaging at 60 fps by frequency up-conversion in DAST crystal"; Proc. SPIE 8964, Nonlinear Frequency Generation and Conversion: Materials, Devices, and Applications XIII, 89640B (Feb. 20, 2014); doi:10.1117/12.2038685;

Fan et al; "Real-time terahertz wave imaging by nonlinear optical frequency up-conversion in a 4-dimethylamino-N'-methyl-4'-stilbazolium tosylate crystal"; Applied Physics Letters, 104, 101106 (2014); doi:10.1063/1.4868134; and Tekavec et al; "Video Rate 3D THz tomography": post-deadline paper, Conference on Lasers and Electro-optics (Jun. 8-13, 2014, San Jose, Calif.); incorporated by reference as if fully set forth herein.

SUMMARY

A terahertz image beam is upconverted by a nonlinear optical process (e.g., sum- or difference-frequency generation with a visible or near IR upconverting beam). The upconverted image is acquired by a visible or near IR image detector. The terahertz image beam and upconverting beam comprise continuous-wave (cw) beams. The bandwidths and center wavelengths of the terahertz image beam and the upconverting beam are such that wavelength filtering can be employed to permit an upconverted image beam to reach the detector while blocking or substantially attenuating the upconverting beam.

Objects and advantages pertaining to upconversion of terahertz images and detection of the upconverted images may become apparent upon referring to the exemplary embodiments illustrated in the drawings and disclosed in the following written description.

This summary is provided to introduce a selection of concepts in a simplified form that are further described below in the Detailed Description. This Summary is not intended to identify key features or essential features of the disclosed or claimed subject matter, nor is it intended to be used as an aid in determining the scope of the claimed subject matter.

BRIEF DESCRIPTION OF THE DRAWINGS

FIG. 4 is a table comparing estimated signal strength of several techniques for acquiring a terahertz image using trains of nanosecond, picosecond, or femtosecond pulses, or continuous-wave (cw) beams.

FIGS. 9A-9C are visible images of three other test objects; FIGS. 10A-10C are raw upconverted terahertz images of those objects in transmission; FIGS. 11A-11C are normalized, upconverted terahertz images of those objects in transmission.

Figure 1:
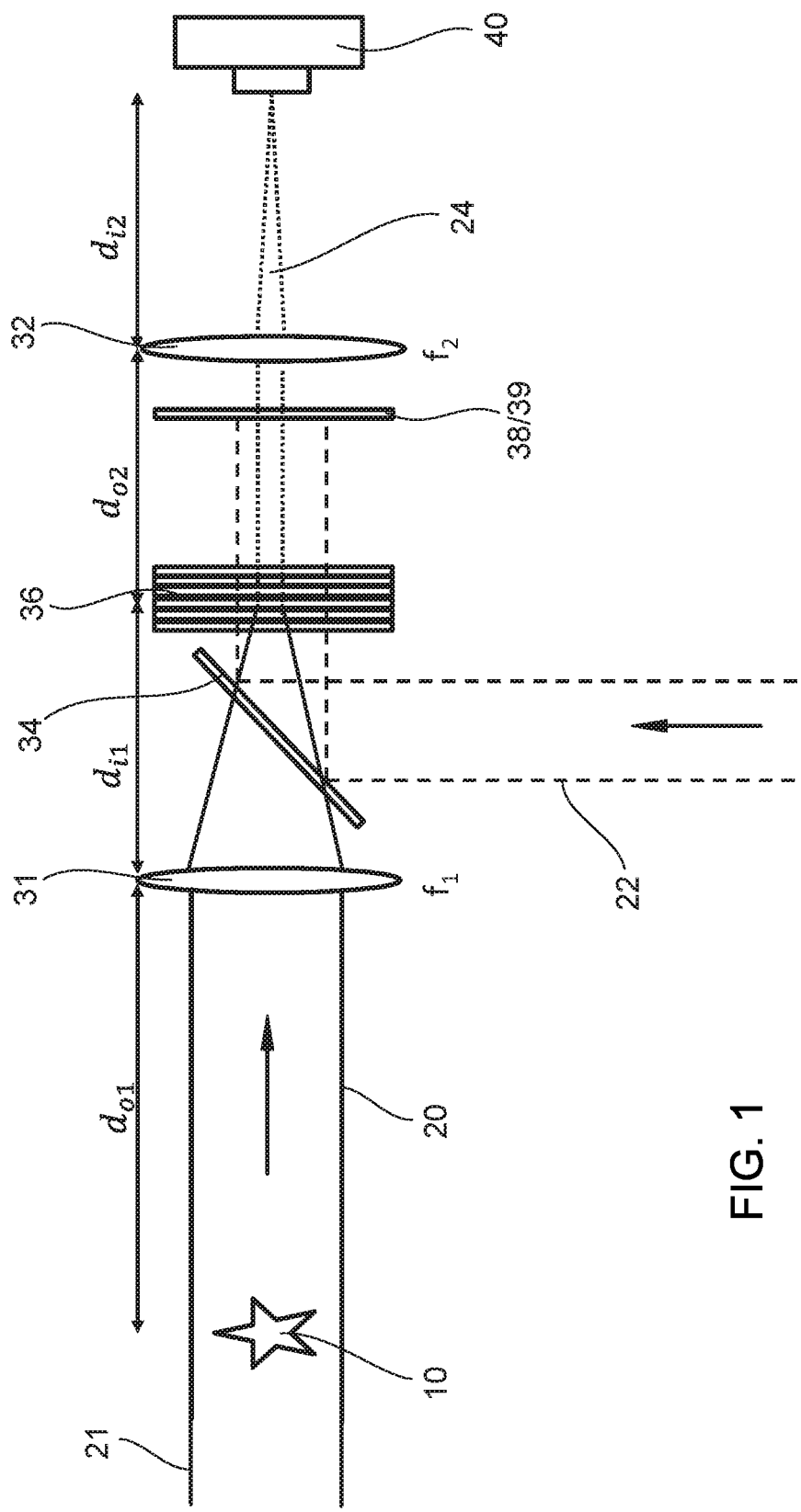
FIG. 1 illustrates schematically a first example of an apparatus for acquiring an upconverted terahertz image.

The embodiments depicted are shown only schematically: all features may not be shown in full detail or in proper proportion, certain features or structures may be exaggerated relative to others for clarity, and the drawings should not be regarded as being to scale. The embodiments shown are only examples: they should not be construed as limiting the scope of the present disclosure or appended claims.

DETAILED DESCRIPTION OF EMBODIMENTS

For purposes of the present disclosure and appended claims, and regardless of use in any cited or incorporated references listed herein, the terms "continuous-wave" and "cw," when NOT followed by the term "modelocked," shall denote an optical or terahertz beam wherein the average power and the peak power are substantially equal to each other. In other words, a continuous-wave or cw beam does not comprise a train of pulses having peak power higher (often orders of magnitude higher) than the average power.

Conversely, the terms "continuous-wave modelocked" and "cw modelocked" shall denote an optical or terahertz beam that comprises a train of pulses having peak power higher than average power and typically having a pulse repetition rate that corresponds to a round trip time of an optical resonator cavity.

The terahertz (THz) wave region of the electromagnetic spectrum (i.e., about 0.05 THz to about 10 THz), a relatively under-developed spectral "gap" between the microwave and long-wave infrared spectral regions, is interesting for several reasons. Many biological and chemical compounds have unique absorption features in this spectral region, making terahertz radiation attractive for imaging in defense, security, biomedical, and industrial settings. Terahertz radiation can pass with little or no attenuation through many substances that are opaque to optical, ultraviolet, or infrared radiation (e.g., ceramics, fabrics, dry organic materials, plastics, paper, or various packaging materials) with little attenuation. Imaging with terahertz radiation enables sub-millimeter spatial resolution, potentially providing higher quality images compared to images obtained at longer wavelengths (e.g., using millimeter waves).

Direct acquisition or detection of images at terahertz frequencies is hampered by the typically low sensitivity or low spatial resolution of suitable detectors (e.g., bolometer, Golay cell, or microbolometer array), by the need for raster scanning to obtain a two-dimensional image if a single-channel detector is used, or by the need for cryogenic cooling of a bolometric detector or array. Sensitive two-dimensional detector arrays with high spatial resolution operable at room temperature (e.g., CCD arrays, CMOS arrays, or InGaAs arrays) are readily available for detecting images in the visible and near infrared (near IR) portions of the electromagnetic spectrum (i.e., wavelengths from about 400 nm to about 3000 nm); the problems noted above for direct detection of terahertz-frequency images could be avoided by using such detectors, however, those detectors are not sensitive to terahertz radiation. Various nonlinear optical effects can be exploited to enable use of visible or near IR detectors or arrays for acquisition of terahertz images.

So-called coherent detection can be employed for acquiring terahertz images using a visible or near IR detector; examples are disclosed in the references of Wu et al, Yonera et al, Jiang et al, and Zhang et al (cited above). The coherent detection method typically employs a short optical pump pulse (e.g., <100 femtoseconds (fs) at a visible or near IR wavelength) to create a broadband THz pulse. Coherent detection of the THz pulse can be achieved by mixing it with a short optical probe pulse (e.g., <100 fs at a visible or near IR wavelength; typically an amplitude-scaled replica of the pump pulse) in an electro-optic crystal. The polarization of the optical probe pulse is rotated by the THz pulse electric field due to the Pockels effect; the amount of rotation is proportional to the THz field amplitude and can be measured by detection through an analyzer polarizer. Coherent detection can be implemented using a single detector element combined with raster scanning of the object or the THz image, or a visible or near IR detector array can be employed (e.g., a CCD camera or CMOS array), thereby eliminating the need for raster scanning. However, image contrast of the acquired images typically is limited by a low signal to noise ratio. In addition, the broad optical frequency bandwidth (typically about 2 to 3 THz) of the THz radiation generated by the short optical pulses often results in significant atmospheric absorption of certain frequencies within that bandwidth, resulting in loss of THz power and distortion of the THz frequency spectrum.

Figure 2:
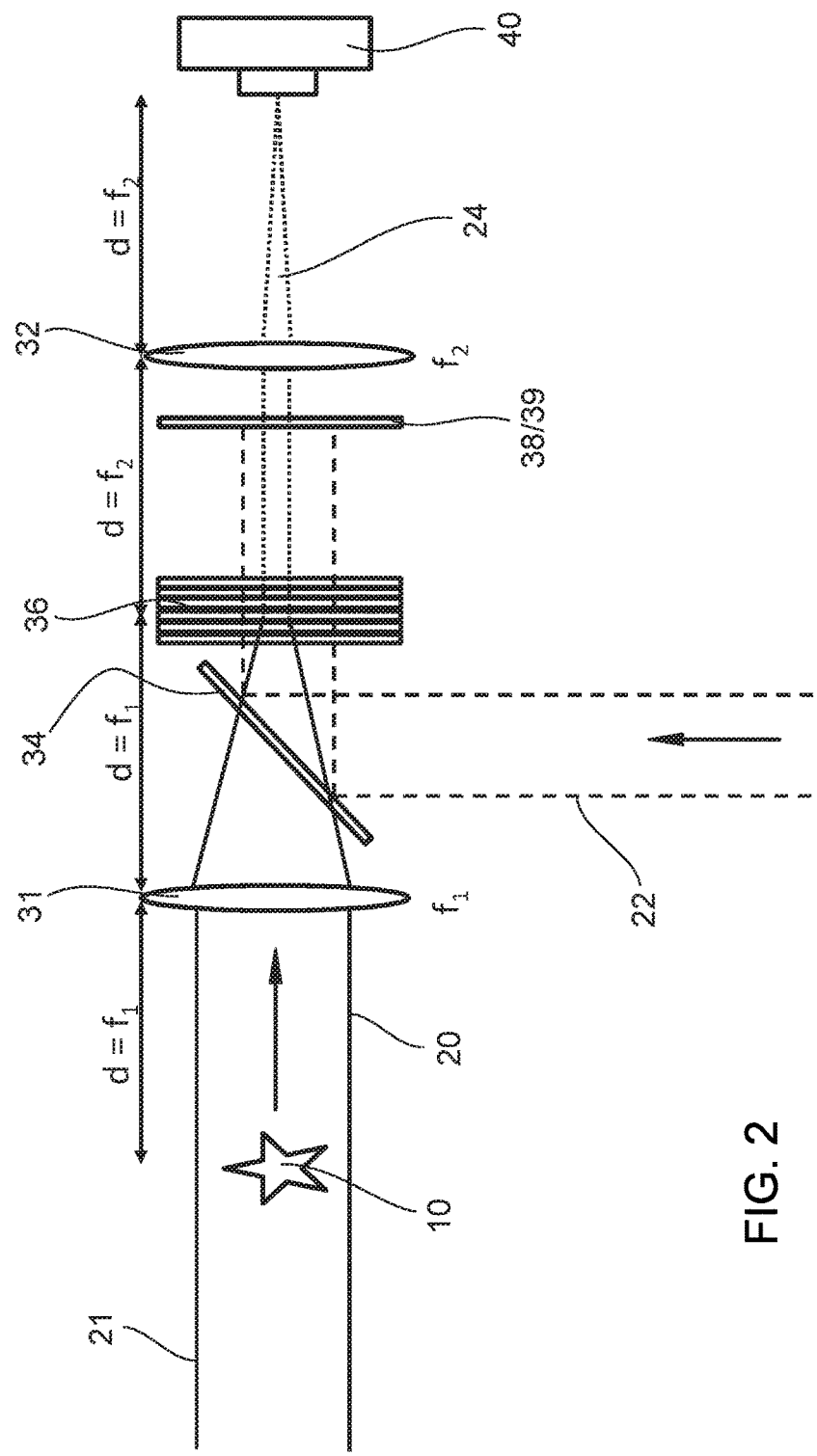
FIG. 2 illustrates schematically a second example of an apparatus for acquiring an upconverted terahertz image.

Disclosed herein is an alternative to coherent detection, in which a visible or near IR detector or array can be employed for acquiring THz images by (i) nonlinear optical upconversion of those images to optical or near infrared wavelengths (i.e., about 400 nm to about 3000 nm) and (ii) detection of the upconverted images using the detector or array. Examples are illustrated schematically in FIGS. 1 and 2 of systems for generating and acquiring upconverted terahertz images. In each example, an object 10 is illuminated by a beam of terahertz radiation (i.e., terahertz imaging beam 21) at a wavelength of $\lambda_{THz}=c/\nu_{THz}$ (c is the speed of light). A terahertz image can be generated by reflection or scattering from the object 10 or by transmission through or around the object 10. The reflected or transmitted terahertz image beam 20 is collected by a first focusing element 31 (shown as a single lens in FIGS. 1 and 2; an off-axis parabolic reflector or other one or more transmissive or reflective focusing elements suitable for terahertz radiation can be employed) and relayed to an upconverting nonlinear optical medium 36. An upconverting beam 22 at a visible or near IR wavelength $\lambda_{UC}$ is combined (usually substantially collinearly) with the terahertz image beam 20 by a beam combiner 34; the beam combiner can be of any suitable type or construction (e.g., a pellicle), and can either reflect the upconverting beam 22 while transmitting the terahertz image beam 20 (as shown in FIGS. 1 and 2), or can transmit the upconverting beam 22 while reflecting the terahertz image beam 20 (not shown).

The terahertz image beam 20 and upconverting beam 22 co-propagate through the upconverting nonlinear optical medium 36, in which one or more upconverted image beams 24 are produced by nonlinear optical interactions (sum- or difference-frequency generation; SFG or DFG, respectively) between the terahertz image beam 20 and the upconverting beam 22. Residual radiation from the upconverting beam 22 is attenuated or blocked by one or more wavelength dependent filters 38 or one or more polarizers 39 (which collectively constitute an image filtering element). The one or more upconverted image beams 24 (at $1/\lambda_{DFG}=1/\lambda_{UC}-1/\lambda_{THz}$ or $1/\lambda_{SFG}=1/\lambda_{UC}+1/\lambda_{THz}$ or both) are collected by a second focusing element 32 (shown as a single lens in FIGS. 1 and 2; any one or more transmissive or reflective focusing elements suitable for the wavelength(s) of the upconverted image beam(s) can be employed) and relayed to a visible or near IR detector array 40 for detection of the upconverted image. Whether any residual radiation from the terahertz image beam 20 reaches the detector array 40 is largely irrelevant, because the terahertz radiation typically would have no discernible effect on the visible or near IR detector array 40. However, the detector array 40 is sensitive to residual radiation from the upconverting beam 22; any such residual upconverting radiation reaching the detector array 40 represents an undesirable background signal for detection of the one or more upconverted image beams 24 (further discussed below).

A detector array 40 is shown and described in the examples, enabling acquisition of entire images by receiving simultaneously different spatial portions of the upconverted image beam on multiple corresponding detector elements of the detector array. However, the present disclosure or appended claims also can encompass use of a single detector element scanned across the upconverted image beam so as to receive sequentially different spatial portions of the upconverted image beam on the single detector element.

The effective focal length (e.g., the focal length of a single lens or single curved mirror, or the effective focal length of a multicomponent focusing element) of the first focusing element 31 is $f_1$; the effective focal length of the second focusing element 32 is $f_2$. In the configuration of FIG. 1, the distance between the object 10 and the first focusing element 31 is $d_{o1}$, the distance between the first focusing element 31 and the nonlinear optical medium 36 is $d_{i1}$, and the object 10, the first focusing element 31, and the nonlinear optical medium 36 are positioned so that $1/d_{o1}+1/d_{i1}=1/f_1$, i.e., the object 10 and the nonlinear optical medium 36 are positioned at conjugate planes defined by the focusing element 31 so that a terahertz image of the object 10 is formed at the nonlinear optical medium 36 with a magnification of $-d_{i1}/d_{o1}$. That terahertz image is upconverted by SFG or DFG with the upconverting beam 22 in the nonlinear optical medium 36. The distance between the nonlinear optical medium 36 and the second focusing element 32 is $d_{o2}$, the distance between the second focusing element 32 and the detector array 40 is $d_{i2}$, and the nonlinear optical medium 36, the second focusing element 32, and the detector array 40 are positioned so that $1/d_{o2}+1/d_{i2}=1/f_2$, i.e., the nonlinear optical medium 36 and the detector array 40 are positioned at conjugate planes defined by the focusing element 32 so that the upconverted image generated in the nonlinear optical medium 36 is reimaged at the detector array 40 with a magnification of $-d_{i2}/d_{o2}$. The overall magnification of the image formed on the detector array 40 relative to the object 10 is $(d_{i1} \cdot d_{i2})/(d_{o1} \cdot d_{o2})$.

In the configuration of FIG. 2, the distance between the object 10 and the first focusing element 31 is $f_1$, and the distance between the first focusing element 31 and the nonlinear optical medium 36 is also $f_1$. As a result, a spatial Fourier transform of the terahertz image is formed at the nonlinear optical medium 36; it is that spatial Fourier transform that is upconverted by SFG or DFG with the upconverting beam 22 in the nonlinear optical medium 36 to generate upconverted spatial Fourier transform(s) of the terahertz image. The distance between the nonlinear optical medium 36 and the second focusing element 32 is $f_2$, and the distance between the second focusing element 32 and the detector array 40 is also $f_2$. As a result, an upconverted image is formed at the detector array 40 from the upconverted spatial Fourier transform generated in the nonlinear optical medium 36. The overall magnification of the image formed on the detector array 40 relative to the object 10 is $-(\lambda_{UC} \cdot f_2)/(\lambda_{THz} \cdot f_1)$. The configuration of FIG. 2 can in some instances lead to a more compact arrangement of the image upconversion system, because often $d_{i1}+d_{i2}+d_{o1}+d_{o2}$ is larger than $2 \cdot (f_2+f_1)$.

In any real system the locations of the object 10, the focusing elements 31 and 32, the nonlinear optical medium 36, or the detector array 40 might deviate from the exact positions given for the two configurations described above. For the purposes of the present disclosure or appended claims, a given imaging arrangement shall be considered to conform to one of those configurations if an upconverted image is formed at the detector array 40 of sufficiently good quality for a given application.

In the two configurations described above, an upconverting focusing element 33 conveys the upconverting beam 22 into the nonlinear optical medium 36 to interact with the terahertz image beam 20. The upconverting beam 22 preferably is made as small as practicable at the nonlinear optical medium 36 (for increased intensity of the upconverting beam resulting in increased upconversion efficiency) while still substantially overlapping spatially the entire terahertz image beam 20 and exhibiting a substantially flat wavefront and sufficiently small spatial intensity variation across the spatial extent of the terahertz image or Fourier transform. To those ends, typically the focusing element 33 (e.g., a single lens, a single curved mirror, a telescope, or a suitable combination of one or more transmissive or reflective focusing components) is arranged to form a relatively gently focused beam waist of the upconverting beam 22 at the nonlinear optical medium 36. For example, a focusing element 33 can be arranged to produce a beam waist about 7 mm wide (full width at half maximum, i.e., FWHM) at the nonlinear optical medium 36; other suitable widths can be employed. The effect of an upconverting beam size that is too small depends on the configuration of the imaging system. In the configuration of FIG. 1, a small upconverting beam 22 can result in loss of peripheral portions of the upconverted image if peripheral portions of the terahertz image are not upconverted. In the configuration of FIG. 2, a small upconverting beam 22 can result in loss of sharpness of the upconverted image if larger wavevector components (i.e., peripheral portions of the spatial Fourier transform) of the terahertz image are not upconverted. In either configuration, deviations from a flat wavefront or uniform intensity of the upconverting beam 22 typically can be tolerated; the magnitude of such deviations that can be tolerated can vary and typically is dependent on the image quality needed or desired for the upconverted image.

Examples are shown in FIGS. 3A-3F of wavelength spectra of the upconverting beam 22 and one or two upconverted image beams 24. In each example one or both upconverted image beams 24 are formed in the nonlinear optical medium 36 by one or both of sum- and difference-frequency generation (SFG and DFG, respectively) between the THz image beam 20 (centered at $\nu_{THz} \approx 1.55$ THz) and the upconverting beam 22 (centered at $\lambda_{UC} \approx 800$ nm in FIG. 3A; centered at $\lambda_{UC} \approx 1064$ nm in FIGS. 3B-3E; centered at $\lambda_{UC} \approx 1550$ nm in FIG. 3F). Depending on the nature of the SFG and DFG nonlinear optical processes, in some instances only one of those processes will produce a corresponding upconverted image beam 24.

Figure 3A:
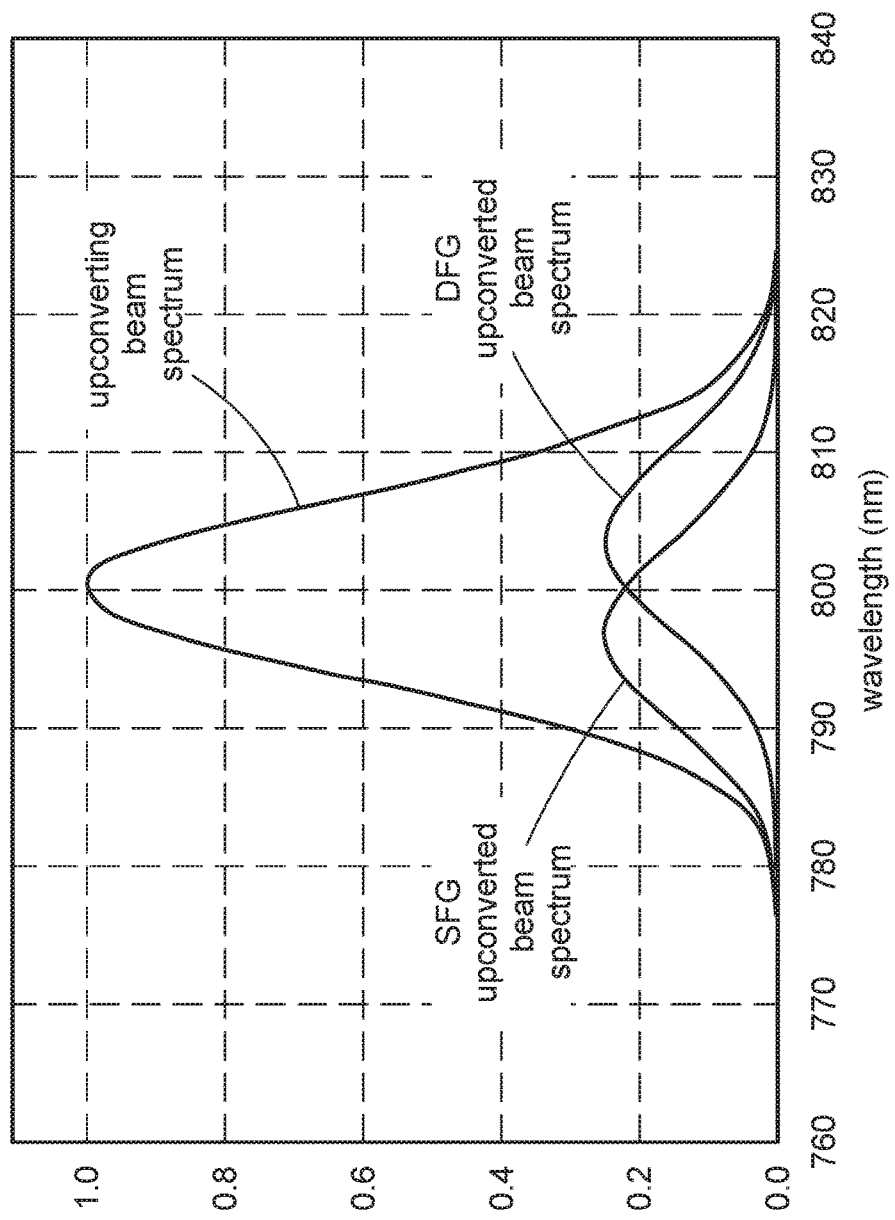
FIGS. 3A-3D and 3F are examples of spectra of an upconverting optical beam and upconverted terahertz image beams, wherein (i) both beams comprise trains of femtosecond pulses (FIG. 3A), (ii) the terahertz imaging beam is a cw beam and the upconverting beam is a train of nanosecond pulses (FIG. 3B), (iii) both beams comprise continuous-wave (cw) beams (FIGS. 3B and 3F), or (iv) both beams comprise trains of picosecond pulses (FIGS. 3C and 3D), before maximal polarization- or wavelength-based filtering.

In previous examples exhibiting spectra similar to those of FIG. 3A (e.g., as disclosed in the above-cited references of Wu et al, Yonera et al, Jiang et al, and Zhang et al), the upconverting beam 22 comprises a train of pulses about 100 fs in duration with a corresponding spectral bandwidth of about 15 nm centered at $\lambda_{UC} \approx 800$ nm. The upconverted image beams 24 have corresponding center wavelengths of $\lambda_{SFG} \approx 796$ nm and $\lambda_{DFG} \approx 804$ nm with similar spectral bandwidths. In this example the upconverted image beams 24 are polarized orthogonally relative to the upconverting beam 22 due to the nature of the nonlinear optical process (e.g., Type I or Type II nonlinear optical processes) employed for SFG and DFG in the nonlinear optical medium 36. In addition to the spatial overlap of the terahertz image beam 20 and the upconverting beam 22 discussed above, substantial temporal overlap of the respective pulse trains of those beams is also necessary for achieving a desired efficiency of upconversion of the terahertz image. A suitable delay line is inserted into the beam paths of one or both of the terahertz image beam 20 or the upconverting beam 22; the delay line can be adjustable to enable optimization of the upconversion efficiency. Shorter pulse duration (ca. 100 fs) enhances the efficiency of the SFG and DFG processes, but the concomitant larger bandwidth (ca. 15 nm) causes substantial spectral overlap of the upconverting beam 22 and the upconverted image beams 24. Because of that overlap, a wavelength dependent filter 38 typically cannot be employed as part of the image filtering element for attenuating the residual upconverting beam 22. Orthogonal polarization of the upconverting beam 22 and the upconverted image beams 24 enables use of a polarizer 39 as the image filtering element for attenuating the residual upconverting beam 22. However, a polarizer will at best exhibit attenuation of about $10^{-6}$ for the blocked polarization state ($10^{-4}$ to $10^{-5}$ is more realistic) and the residual upconverting beam 22 typically is not in a pure linear polarization state due to passage through the nonlinear optical medium 36 and various other optical components. The portion of the residual upconverting beam 22 that leaks through the polarizer 39 often can be substantially more intense than the upconverted image beams 24. In addition, the broad optical frequency bandwidth of the THz image beam 20 suffers from significant atmospheric absorption of certain frequency components, as noted above. For all these reasons, pulses of such short duration (a few hundred femtoseconds or shorter with correspondingly large spectral bandwidth) are not particularly well suited for upconversion of terahertz images.

Figure 3B:
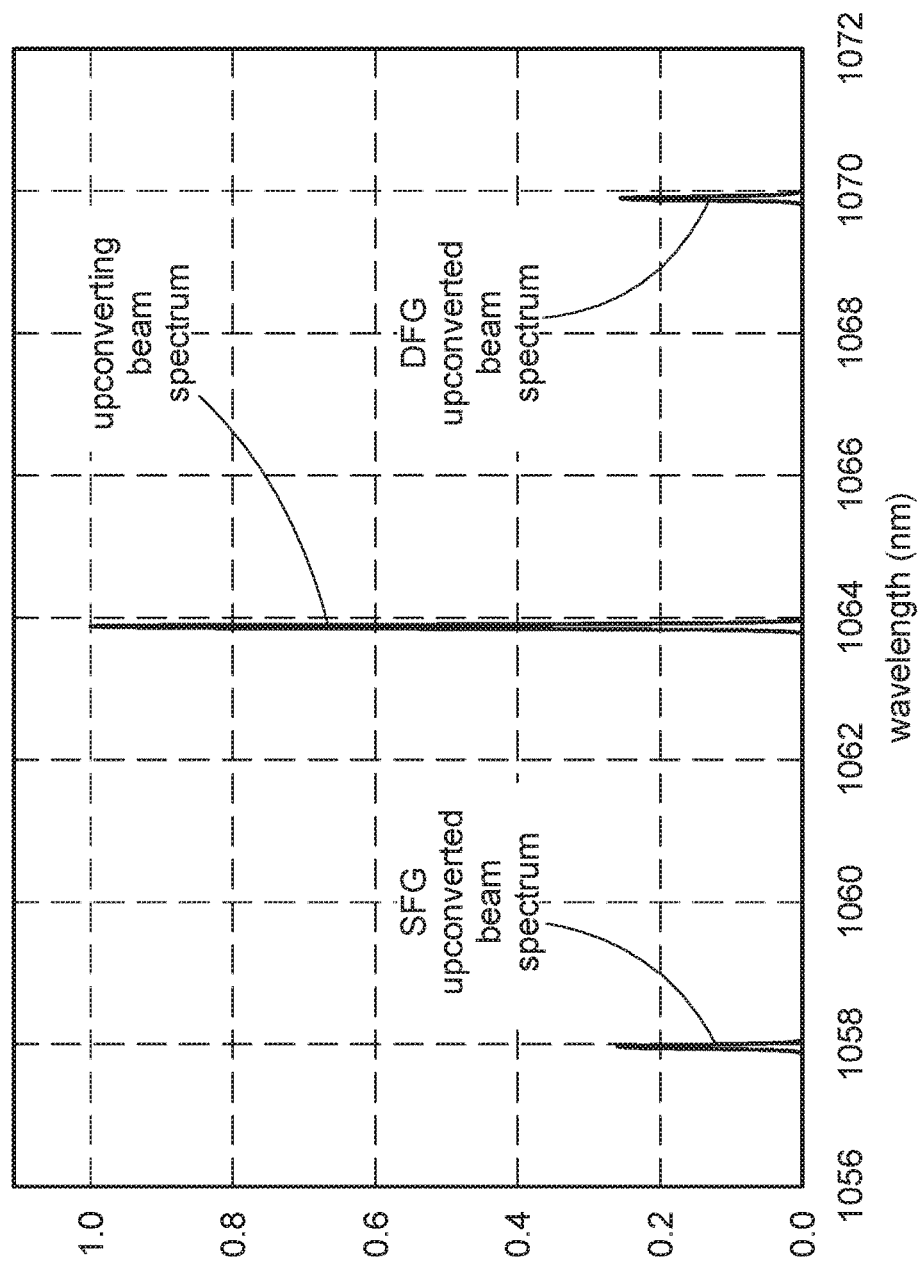

In various other previous examples (e.g., those disclosed in the references of Khan et al, Nahata et al, Cao et al, and Ding et al, cited above; representative spectra shown in FIG. 3B with $\lambda_{UC} \approx 1064$ nm, $\lambda_{SFG} \approx 1058$ nm, and $\lambda_{DFG} \approx 1070$ nm), a continuous-wave terahertz beam, and an upconverting beam that comprises pulses that are several nanoseconds (ns) in duration with correspondingly narrow spectral bandwidth (e.g., <0.1 nm), are employed, thereby enabling a wavelength dependent filter to be employed in the image filtering element for attenuating residual upconverting radiation before detection of the upconverted signal. However, the longer pulses require pulse energy of the upconverting beam to be close to the damage threshold of the nonlinear optical medium 36 to achieve detectable upconversion of the terahertz image. Such pulse energies typically are only available in low repetition rate pulsed lasers (e.g., pulse repetition rates on the order of 10 Hz), however, pulse-to-pulse fluctuations tend to obscure detection of the small signal level of the upconverted image. Most detector arrays are sensitive to average power, which is quite low at such low repetition rates. The repetition rate is also comparable to desired frame rates for near-real-time video imaging and is therefore not well-suited to that application; video-rate imaging would require a single shot per frame. In addition, the upconverting beam typically must include radiation at the desired DFG wavelength to enable detection of the upconverted image, making that detection an inherently nonzero-background process (e.g., as in the reference of Cao et al). For all of these reasons, pulses of such long duration (several nanoseconds or longer with correspondingly narrow spectral bandwidth) and such large pulse energy are not particularly well suited for upconversion of terahertz images.

In an example disclosed by Kozlov et al (US 2015/0153234; example spectrum shown in FIG. 3C), the terahertz image beam 20 and the upconverting beam 22 comprise trains of pulses about 6-10 picoseconds (ps; FWHM) in duration, the upconverting beam is about 0.3 nm in bandwidth (FWHM), and the terahertz image beam is similarly narrow in its frequency spectrum (e.g., less than 100 GHz (FWHM) centered at about 1.55 THz, thus enabling substantial avoidance of atmospheric absorption bands). With the upconverting beam 22 centered at $\lambda_{UC} \approx 1064$ nm, the upconverted image beams 24 have corresponding center wavelengths of $\lambda_{SFG} \approx 1058$ nm and $\lambda_{DFG} \approx 1070$ nm and similarly narrow spectral bandwidths. As in the previous example, the upconverted image beams 24 are polarized orthogonally relative to the upconverting beam 22 due to the nature of the nonlinear optical process (e.g., Type I or Type II nonlinear optical processes) employed for SFG and DFG in the nonlinear optical medium 36. Orthogonal polarization of the upconverting beam 22 and the upconverted image beams 24 enables use of a polarizer 39 in the image filtering element for attenuating the residual upconverting beam 22. Longer pulses relative to the example of FIG. 3A results in reduced peak intensities and reduced efficiency of the SFG and DFG processes, although those processes are still more efficient than in the example of FIG. 3B. However, the correspondingly smaller spectral bandwidth substantially eliminates spectral overlap of the upconverting beam 22 and the upconverted image beams 24, enabling use of one or more wavelength dependent filters 38 in the image filtering element, instead of or in addition to polarizer 39, for attenuating the residual upconverting beam 22. A combination of one or more wavelength dependent filters 38 and the polarizer 39 can conservatively yield attenuation of the residual upconverting beam 22 on the order of $10^{-8}$ and perhaps as much as $10^{-10}$ or $10^{-12}$. Alternatively, the lack of spectral overlap of the upconverting beam 22 with the upconverted image beams 24 can enable elimination of the polarizer 39 from the image filtering element and use of alternative, potentially more efficient, nonlinear optical processes in the nonlinear optical medium 36, e.g., a Type 0 nonlinear optical process wherein all polarizations are parallel to one another. The pulse duration also enables terahertz image acquisition to be combined with terahertz tomographic techniques to acquire images originating from differing depths within a sample with spatial resolution on the order of several millimeters.

Figure 3C:
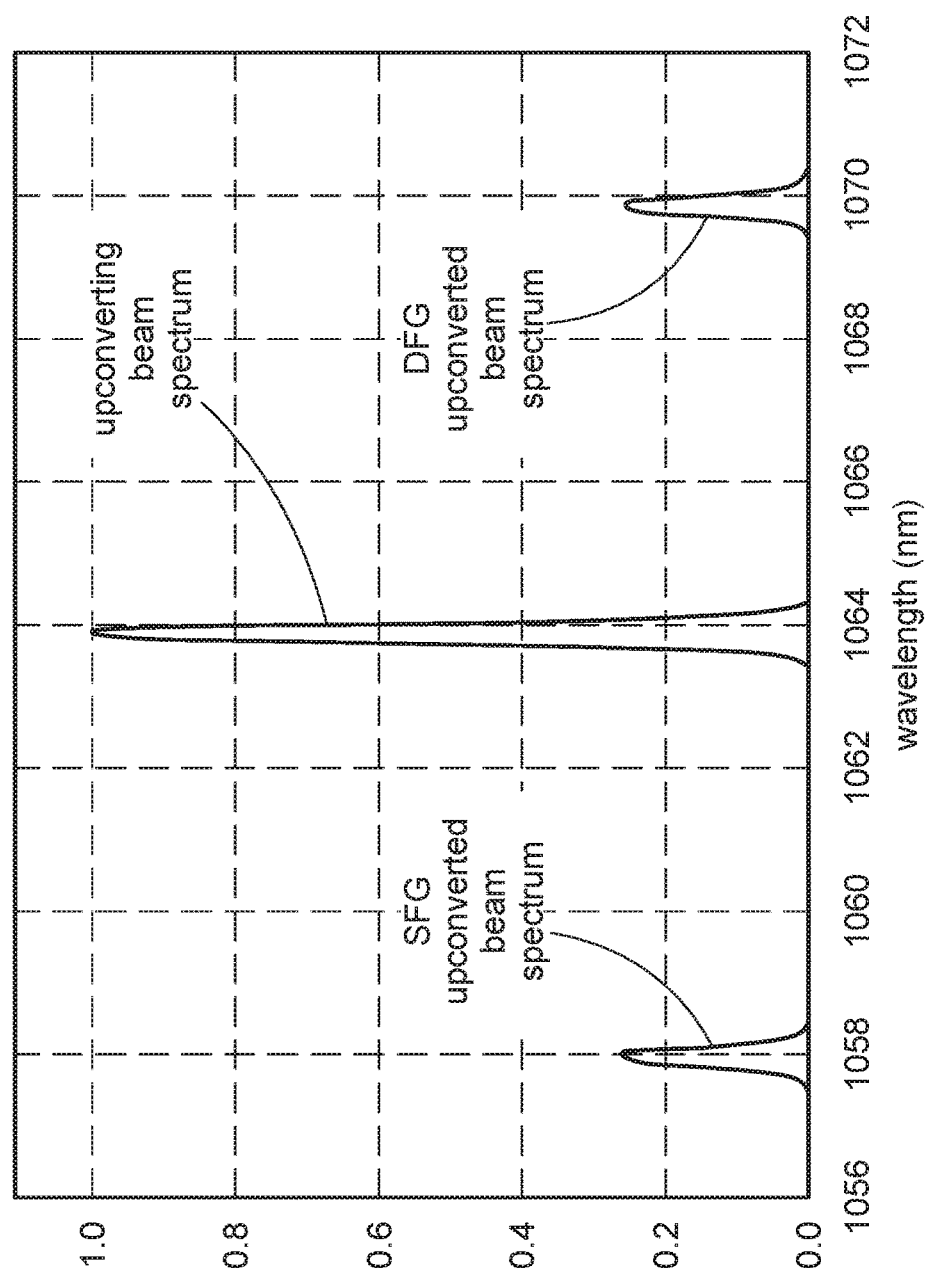
Figure 3D:
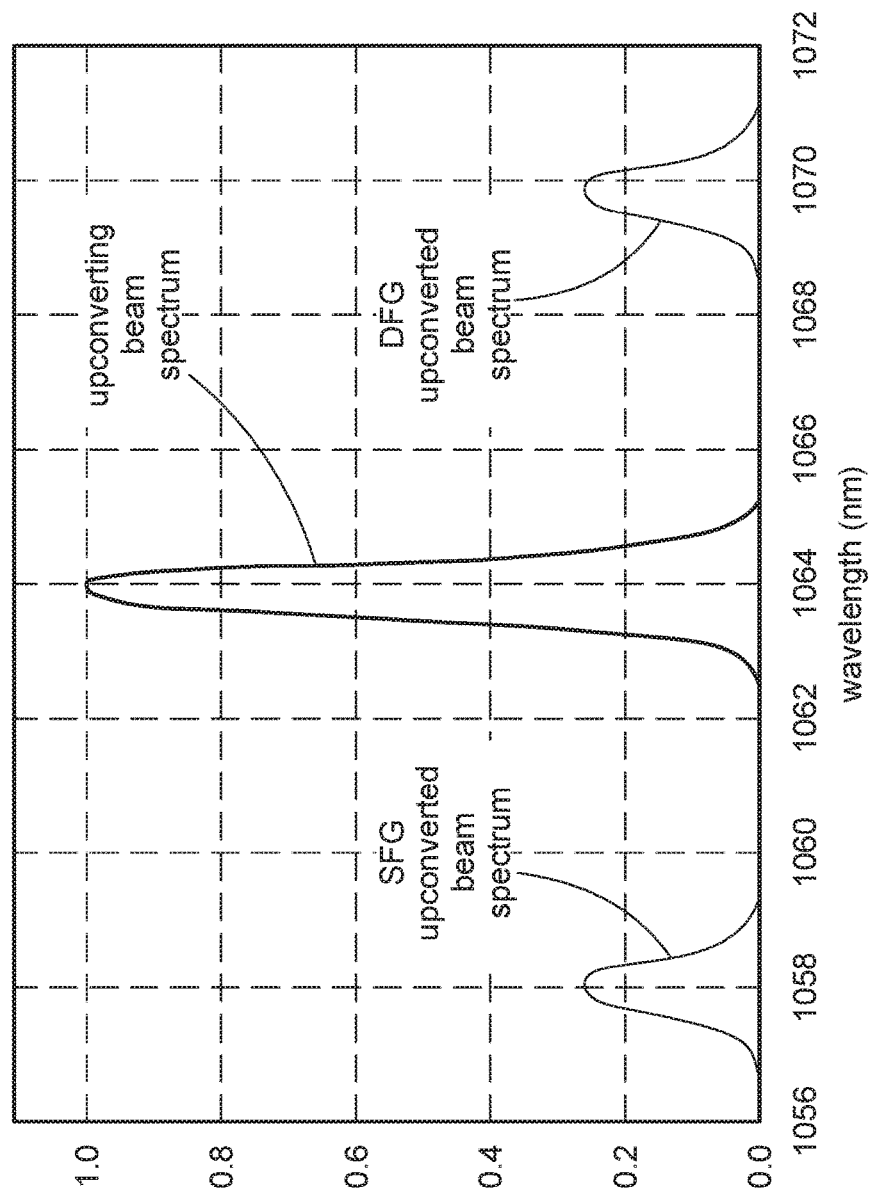

Another example disclosed by Kozlov et al (FIG. 3D) is similar to that of FIG. 3C, except that the pulses employed are about 1-2 ps in duration (FWHM) with a bandwidth of about 1 nm (FWHM). Those parameters can increase the efficiency of the terahertz image upconversion (higher intensity due to shorter pulse duration) while still enabling effective wavelength-based filtering of the residual upconverting beam. The shorter pulse duration also enables improved spatial resolution (e.g., on the order of a millimeter) when terahertz image acquisition is combined with terahertz tomographic techniques to acquire images originating from differing depths within a sample.

In another example disclosed by Kozlov et al, the terahertz image beam can be centered at about 0.85 THz with spectral width similar to one of the preceding examples (enabling substantial avoidance of atmospheric absorption bands). If the upconverting beam is centered at about $\lambda_{UC} \approx 1064$ nm with similar spectral width, the upconverted image beams will have corresponding center wavelengths of $\lambda_{SFG} \approx 1061$ nm and $\lambda_{DFG} \approx 1067$ nm and similar spectral widths. The smaller spectral separation between the upconverting beam and the upconverted image beams may require a polarizer or enhanced spectral filtering for adequate attenuation of the upconverting beam.

Figure 5:
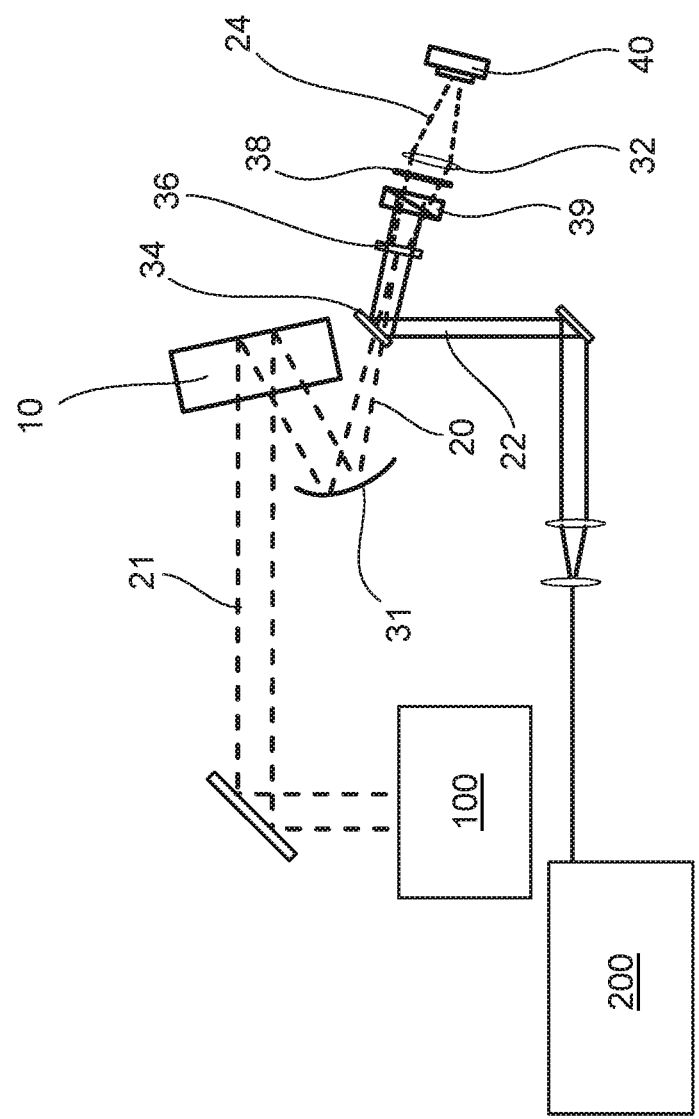
FIG. 5 illustrates schematically an example arrangement of a cw terahertz imaging beam reflected from a sample and upconverted by a cw upconverting beam.

In an inventive example according to the present disclosure, both the terahertz imaging beam 21 (and therefore also the terahertz image beam 20) and the upconverting beam 22 are continuous-wave (cw) beams (FIGS. 1, 2, and 5). Use of cw beams would at first appear to be undesirable; pulsed beams are typically employed (as in the previous examples disclosed above) to exploit the concomitant higher peak powers to drive the nonlinear optical upconversion process. However, higher power cw terahertz sources (e.g., producing average power on the order of 0.1 W to 1 W over frequency ranges from about 0.05 THz to about 0.4 THz, up to about 1.5 THz, or up to about 3 THz) can be employed that deliver power in the cw terahertz image beam 20 comparable to peak powers in the previous examples. However, the much higher duty cycle of the cw terahertz image beam 20 and the upconverting beam 22 (i.e., unity for cw beams versus on the order of $10^{-4}$ for picosecond pulses at typical modelocked source repetition rates) results in comparable or larger average upconverted average power in the upconverted image beam 24. Imaging detectors 40 typically employed are sensitive to average power in the upconverted image beam 24. An example apparatus is schematically illustrated in FIG. 5, wherein a cw terahertz source 100 produces the terahertz imaging beam 21 and a cw visible or near-IR source 200 produced the upconverting beam 22. In the examples of FIGS. 1 and 2, the terahertz image is formed by transmission through or around the object 10; in the example of FIG. 5, the terahertz image is formed by reflection or scattering from the object 10. Typical spectra would resemble the examples of FIG. 3B ($v_{THz}$≈1.55 THz, $\lambda_{UC}$≈1064 nm, $\lambda_{SFG}$≈1058 nm, and $\lambda_{DFG}$≈1070 nm) or FIG. 3F ($v_{THz}$≈0.3 THz, $\lambda_{UC}$≈1550 nm, $\lambda_{SFG}$≈1547.6 nm, and $\lambda_{DFG}$≈1552.5 nm). The average terahertz power and upconverting beam powers of the continuous-wave beams 20 and 22 result in sufficient power in the upconverted image beam 24 (see the table of FIG. 4) to enable near-real-time terahertz imaging, e.g., video-rate terahertz imaging at frame rates of about 5-30 FPS or more. It has been observed that the upconverted image signal varies substantially linearly with terahertz imaging beam power and with upconverting beam power, without evidence of saturation. This suggests that further increases in upconverted image signal can be achieved by further increasing terahertz and upconverting beam powers.

Any suitable source 100 of the continuous-wave (cw) terahertz imaging beam 21 can be employed that produces sufficient power over the desired terahertz frequency range. Some examples exploit the so-called backward-wave oscillator (BWO) effect, and include Terasource tubes produced by Terasense® Group, Inc. Such sources can provide terahertz average power from about 0.1 W up to about 1.0 W over terahertz frequencies from about 0.08 THz up to about 0.36 THz; other suitable sources can be employed. A BWO-type or other terahertz source can be combined with a terahertz amplifier of any suitable type (extant or future-developed; e.g., an 0.85 THz amplifier developed by Northrop Grumman) to provide higher upconverting average power. One or more terahertz sources can be used in combination with one or more frequency doublers or triplers (or both) to extend the accessible terahertz frequency range, e.g., as disclosed in U.S. Pat. No. 8,035,083 issued to Kozlov et al, which is incorporated by reference. Those examples or any other suitable continuous-wave terahertz sources, now extant or future-developed, can be employed as the cw terahertz source 100 within the scope of the present disclosure or appended claims.

Any suitable source 200 of the visible or near infrared upconverting beam 22 can be employed that produced sufficient power at the desired upconverting wavelength and with sufficiently small upconverting bandwidth. Typical sources 200 include solid state, semiconductor, or fiber lasers operating in the visible or near infrared. Examples include Koheras® BOOSTIK single-frequency fiber lasers available from NKT Photonics A/S, which can produce up to about 15 W of upconverting average power at upconverting wavelengths between about 1030 nm and about 1090 nm, or up to about 10 W of upconverting average power at upconverting wavelengths between about 1530 nm and about 1575 nm. Those examples or any other suitable continuous-wave visible or near infrared sources, now extant or future-developed, can be employed as the cw upconverting source 100 within the scope of the present disclosure or appended claims.

Corresponding upconverting bandwidths can be as small as a few tens of kHz in the example upconverting sources 200 described above. Typically the upconverting bandwidth is less than about 0.1 nm, which corresponds to about 30 GHz for $\lambda_{UC}$≈1000 nm or about 20 GHz for $\lambda_{UC}$≈1500 nm. The upconverting bandwidth therefore can impose a lower limit on the terahertz frequency employed while keeping the upconverting beam 22 and the upconverted image beams 24 spectrally separated. However, even if the upconverting bandwidth is exceedingly narrow (as with the example sources described above) so that the upconverting spectrum and the upconverted image spectra do not overlap and are completely separated, their close spacing resulting from use of relatively low terahertz frequencies (e.g., separation of only about 2 nanometers or less for terahertz frequencies less than about 0.3 THz) can nevertheless result in insufficient (or at least problematic) rejection of the upconverting beam 22 while transmitting one or both upconverted image beam(s) 24, or insufficient transmission of the upconverted image beams 24 while substantially rejecting the upconverting beam 22 (discussed further below).

Any suitable nonlinear optical medium 36 can be employed for generating the upconverted image beam(s) 24. One suitable medium comprises a stack of two or more optically contacted gallium arsenide (GaAs) or gallium phosphide (GaP) plates. The thickness of the plates is selected to result in quasi-phase-matched upconversion by the upconverting beam 22 of the terahertz image beam 20 to the one or more upconverted image beams 24. In one example, a stack of 6 to 12 GaAs plates, each about 300 µm thick, can be employed to produce the upconverted image beams 24 at 1058 nm and 1070 nm from the terahertz image beam 20 at about 1.55 THz and the upconverting beam 22 at about 1064 nm, with the polarization of upconverting beam 22 substantially orthogonal to that of upconverted beam(s) 24. More plates can result in higher upconversion efficiency, but the difficulty of maintaining sufficiently high optical quality increases with increasing numbers of plates. In another example, a single GaAs plate up to about 8 to 9 mm thick (i.e., less than or about equal to the coherence length for the upconversion process) can be employed to produce the upconverted image beams 24 at about 1547.6 and about 1552.4 from the terahertz image beam 20 at about 0.3 THz and the upconverting beam 22 at about 1550 nm and polarized orthogonally with respect to the upconverted image beams 24. Other plate numbers or thicknesses can be employed for other combinations of terahertz frequency and upconverting wavelength. Any other suitable nonlinear optical material(s) can be employed, any other suitable phase-matching or quasi-phase-matching schemes can be employed, and any suitable nonlinear optical process, e.g., Type 0, I, II, and so forth, can be employed.

Figure 3E:
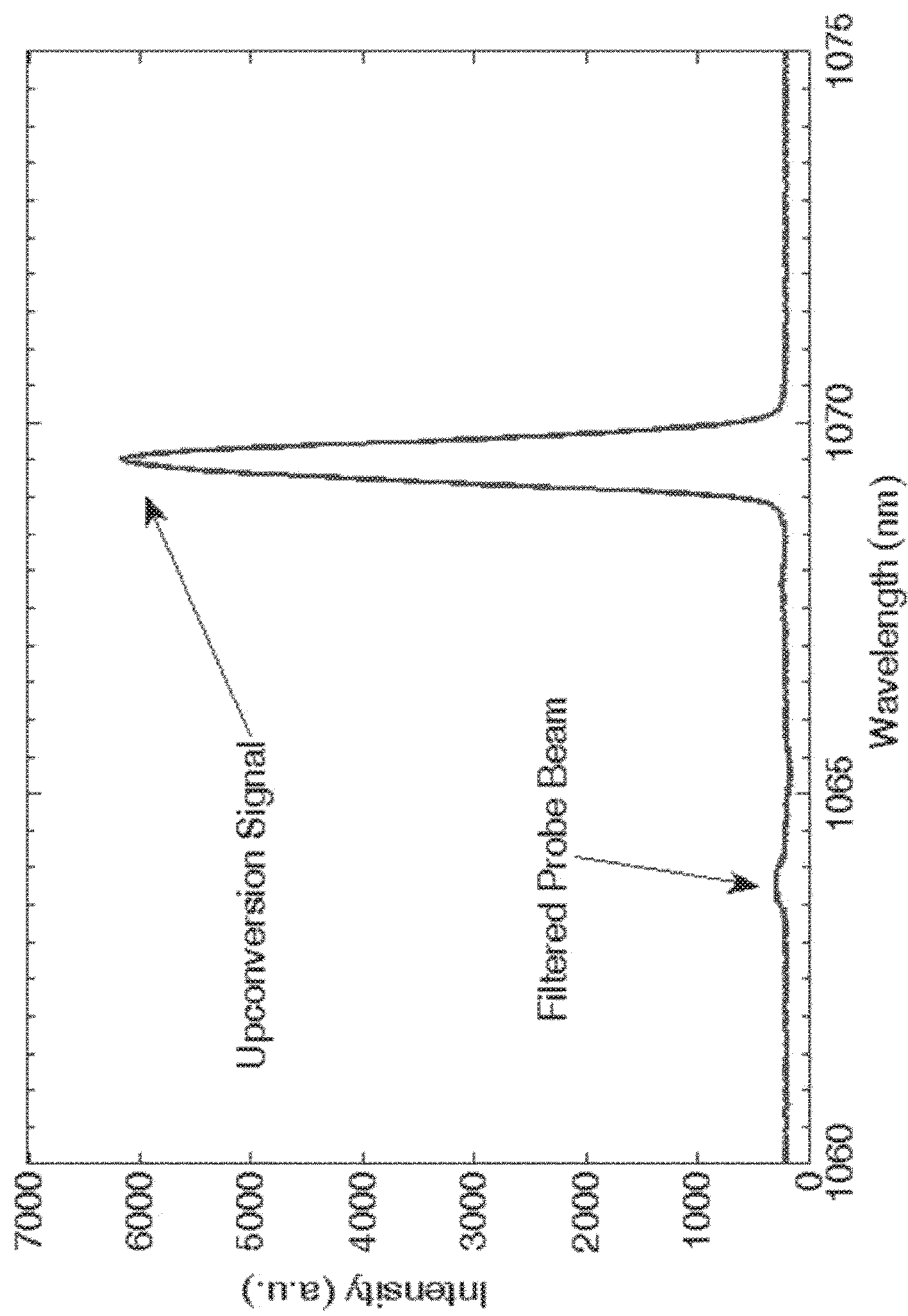
FIG. 3E is an example of polarization- and wavelength-filtered spectra of an upconverted terahertz image beam and a residual upconverting optical beam using picosecond pulses.
Figure 3F:
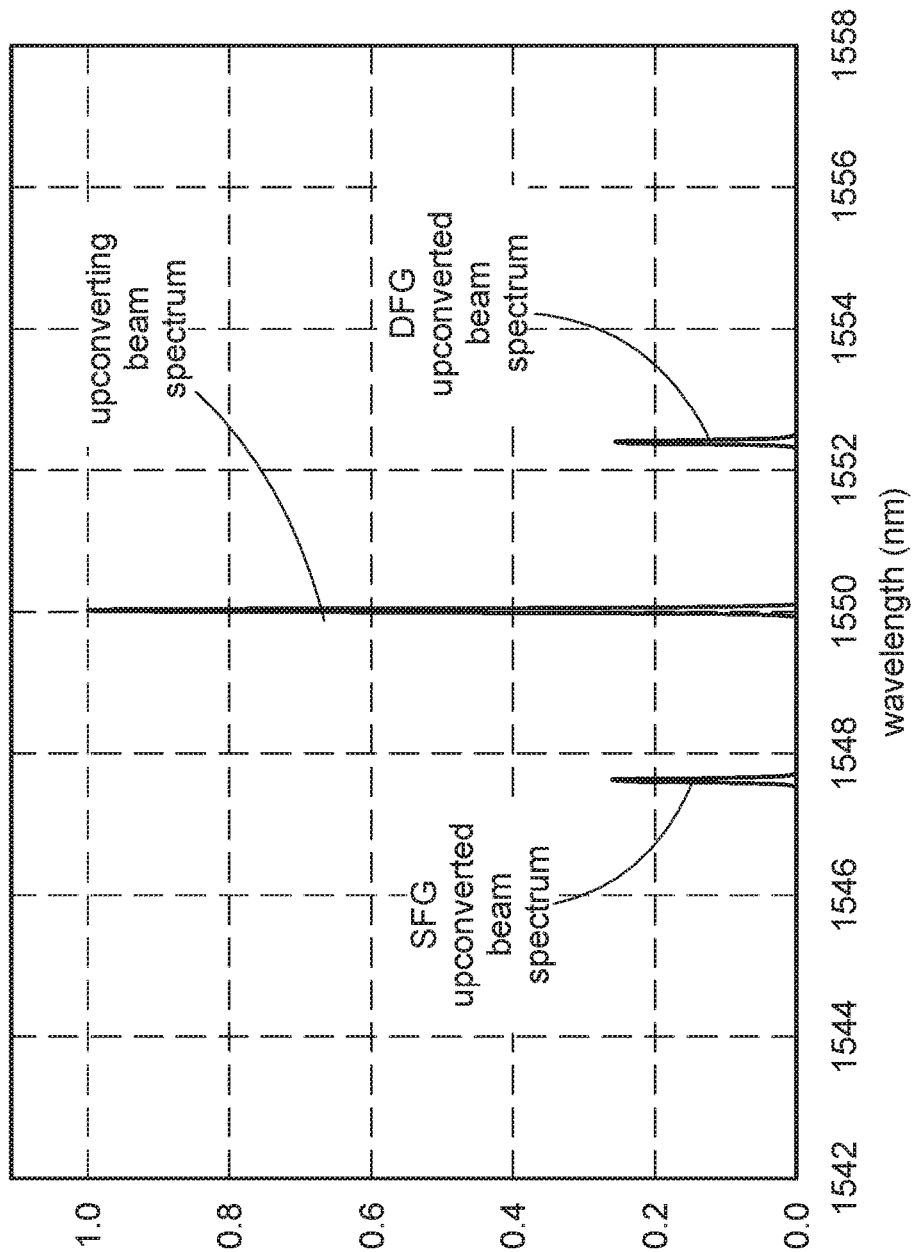

If the nonlinear optical process in the medium 36 produces only one upconverted image beam 24, or if only one of multiple upconverted image beams 24 is desired to be detected at the detector array 40, then a short-pass or long-pass cutoff filter 38 can be employed that attenuates or blocks the upconverting beam 22 while enabling at least a portion (spectrally) of one upconverted image beam to reach the detector 40. For example, a long-pass filter 38 with a cutoff wavelength between the upconverting wavelength and the difference-frequency wavelength can be employed that would attenuate or block the residual upconverting beam 22 at the upconverting wavelength and the upconverted image beam 24 at the sum-frequency wavelength (if present), but would transmit to the detector array 40 at least a portion of the upconverted image beam 24 at the difference-frequency wavelength; an example of a spectrum transmitted by such an arrangement is shown in FIG. 3E for one of the examples disclosed by Kozlov et al. Similarly, a short-pass filter 38 with a cutoff wavelength between the upconverting wavelength and the sum-frequency wavelength could be used to enable the upconverted image beam at the sum-frequency wavelength to reach the detector array 40 while attenuating or blocking the residual upconverting beam 22 at the upconverting wavelength and the upconverted image beam 24 at the difference-frequency wavelength (if present).

In another example, a so-called notch filter 38 (e.g., a Bragg filter or a multilayer thin film interference-type filter) nominally centered at the upconverting wavelength could be employed to attenuate or block the residual upconverting beam 22 while enabling at least portions (spectrally) of both upconverted beams 24 to reach the detector 40. In practice, a thin film notch filter suitable for the particular combination of wavelengths shown in FIG. 3B, 3C, 3D, or 3F may not provide sufficient discrimination between the upconverting beam 22 and upconverted image beam 24, i.e., currently it is difficult to design and manufacture such a thin film notch filter with a sufficiently narrow rejection bandwidth that exhibits both sufficient attenuation of the residual upconverting beam 22 and sufficient transmission of the upconverted image beams 24 at those wavelengths. Also, depending on the nature of the source of the upconverting beam 22, its spectrum can in some instances exhibit excess bandwidth or unwanted sidebands; that issue can in some instances be mitigated by use of a bandpass filter (used in transmission) or a notch filter (used in reflection) centered at $\lambda_{UC}$ to "clean up" the spectrum of the upconverting beam 22. In any case, currently available notch filters can be suitably employed for other, more widely separated combinations of wavelengths, or a future notch filter of improved design and performance could be employed with the combination of wavelengths of FIG. 3B, 3C, 3D, or 3F.

Instead of, or in addition to, one or more thin film filters, one or more Bragg filters can be employed for reducing transmission of the upconverting beam 22 to the imaging detector array 40. Bragg-type notch filters typically exhibit spectral rejection bandwidths narrower than those of thin film notch filters. Suitable examples of such Bragg filters include, e.g., BragGrate™ Raman filters produced by OptiGrate Corporation, Bragg filters disclosed in U.S. Pat. No. 6,673,497 issued to Elimov et al (which is incorporated by reference as if fully set forth herein), or crystalline colloidal Bragg filters such as those disclosed in Asher et al, Spectroscopy Vol. 1 No. 12 p. 26 (1986) (which is incorporated by reference as if fully set forth herein). Such Bragg filters can provide adequate discrimination between the upconverted image beam 24 and the upconverting beam 20, even if relatively low terahertz frequencies are employed that result in relatively close spacing of the upconverting spectrum and the upconverted image spectra (e.g.: separation of about 2 to 3 nanometers or less for terahertz frequencies less than about 0.3 THz, e.g., as in FIG. 3F; or separation less than about 1 nanometer for terahertz frequencies less than about 0.1 THz). Instead or in addition, other types of wavelength dependent filters (e.g., such as those employed in DWDM optoelectronic telecommunications systems) can be employed for discriminating between the upconverted image beam 24 and the residual upconverting beam 20.

A polarizer 39 of any suitable type can be employed if the beams 22 and 24 are orthogonally polarized, instead of or (more typically) in addition to the one or more filtering elements 38 (short pass, long pass, or notch). Any suitable one or more polarizers or one or more spectral filtering elements, extant or future developed, can be employed within the scope of the present disclosure or appended claims. In instances of relatively close spacing of the upconverting spectrum and the upconverted image spectra, one or more polarizers 39, used instead of or in addition to the one or more wavelength dependent filters 38, can provide adequate discrimination between the upconverting beam 22 and the upconverted image beam 24. Whatever filtering arrangement is employed, with spectral separation between the beams 22 and 24 of only a few nanometers or less, transmission of the upconverting beam 22 can in some instances be on the order of one part in $10^6$, one part in $10^7$, or one part in $10^8$, while in other instances the more desirable one part in $10^{10}$ or one part in $10^{12}$ can be achieved (as with the relatively larger spectral separations described above).

Note that even if only one upconverted image beam 24 is to be acquired at the detector array 40, producing the DFG upconverted image beam 24 can be advantageous. Each SFG photon is produced at the expense of a corresponding terahertz photon lost from the terahertz image beam 20; the intensity of the SFG upconverted image beam 24 is therefore limited by the number of photons available in the terahertz image beam 20. In contrast, each DFG photon produced in the upconverted image beam 24 also results in a new photon produced in the terahertz image beam 20. The intensity of the DFG upconverted image beam 24 is therefore limited by the (much larger) number of photons available in the upconverting beam 22. Consequently, if only one upconverted image is to be acquired, it may be desirable to employ DFG to generate that upconverted image. However, generation of the DFG upconverted image beam 24 makes available additional photons in the terahertz image beam 20 for SFG. Even if the DFG upconverted image beam 24 is attenuated or blocked by the filter 38 and only the SFG upconverted image beam 24 reaches the detector array 40, generation of the DFG upconverted image beam 24 can increase the detected intensity of the SFG upconverted image beam 24.

Note that simultaneous SFG and DFG described in the previous paragraph only arises under certain conditions. In the examples described herein, the acceptance bandwidth of the quasi-phase-matched SFG and DFG processes is sufficiently large that both processes can occur with near optimal efficiency for the combination of $\lambda_{UC} \approx 1064$ nm, $\lambda_{SFG} \approx 1058$ nm, and $\lambda_{DFG} \approx 1070$ nm shown in the examples of FIGS. 3B through 3D, or for the combination of $\lambda_{UC} \approx 1550$ nm, $\lambda_{SFG} \approx 1547.6$ nm, and $\lambda_{DFG} \approx 1552.4$ nm shown in the example of FIG. 3F. For more widely separated SFG and DFG wavelengths (i.e., for higher terahertz frequencies), or for a nonlinear optical medium with a smaller acceptance bandwidth, it may not be possible to produce both SFG and DFG upconverted image beams 24.

Figure 8A:
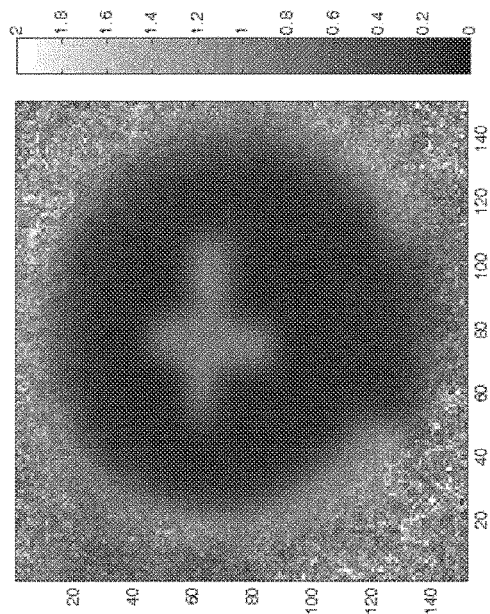
FIGS. 8A-8C are normalized, upconverted terahertz images of those objects in transmission.
Figure 6A:
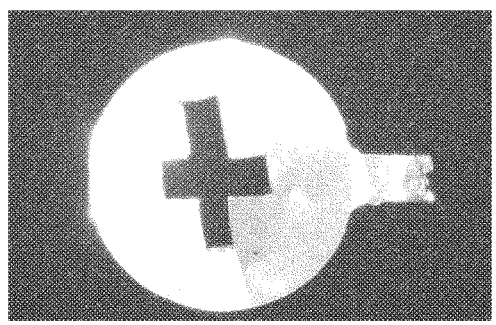
FIGS. 6A-6C are visible images of three test objects.
Figure 7A:
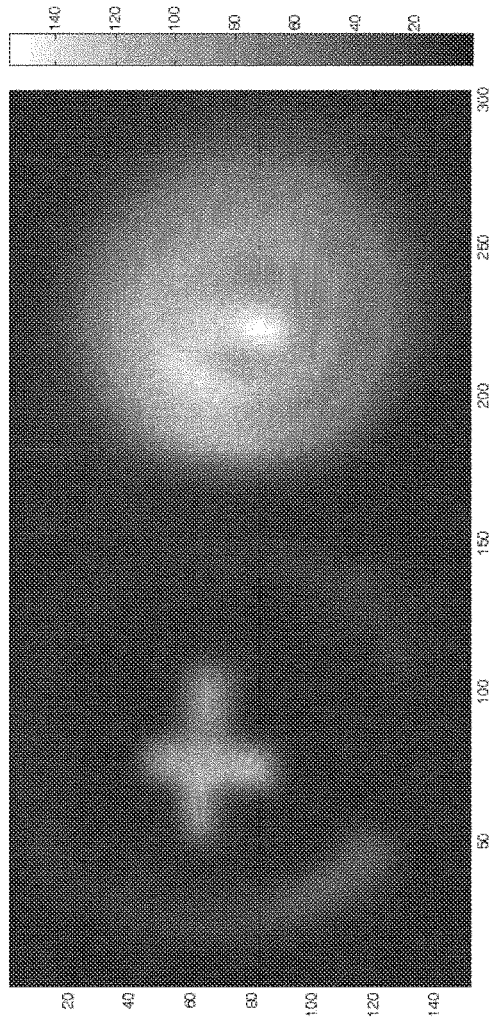
FIGS. 7A-7C are raw upconverted terahertz images of those objects in transmission.
Figure 6B:
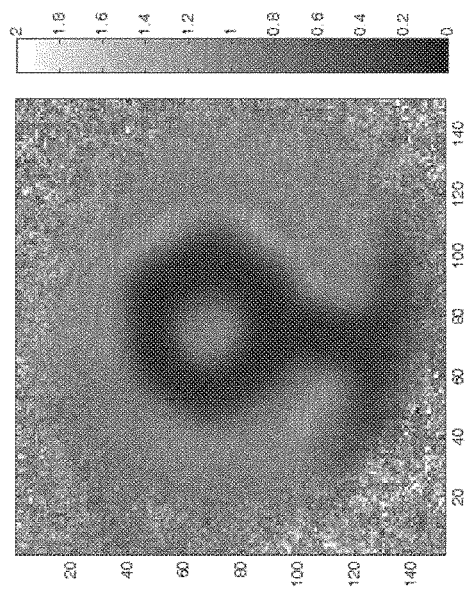
Figure 8B:
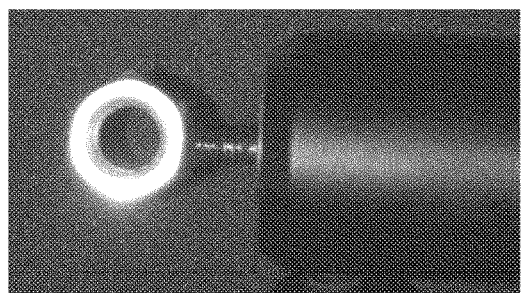
Figure 7B:
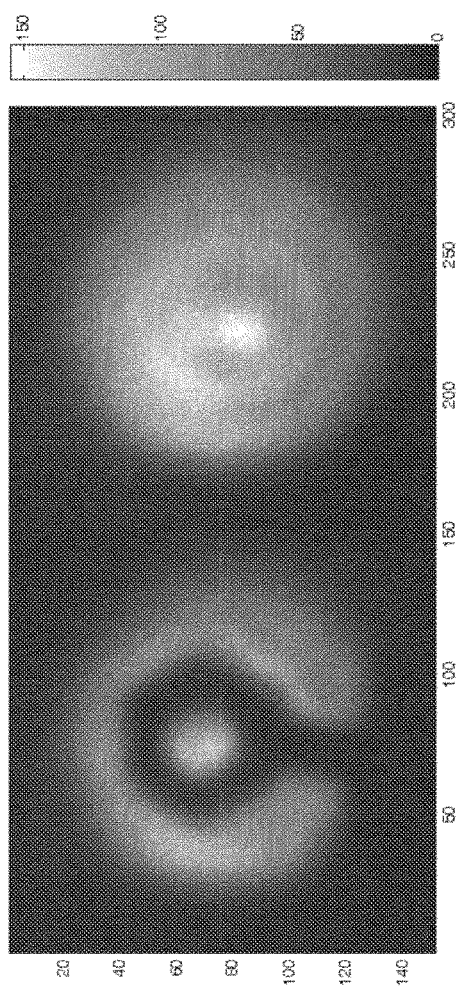
Figure 8C:
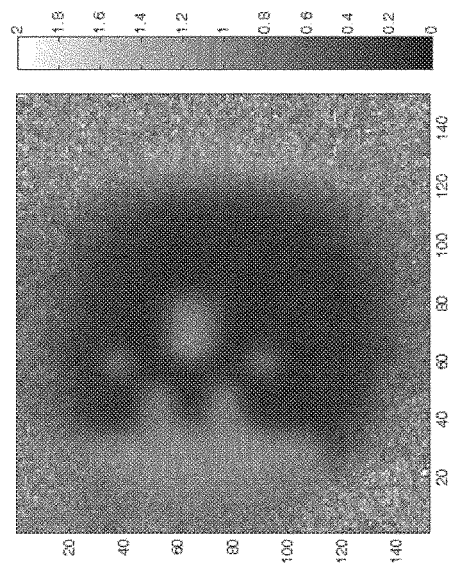
Figure 6C:
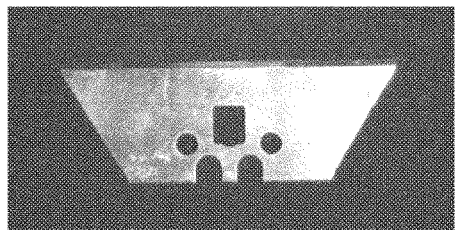
Figure 7C:
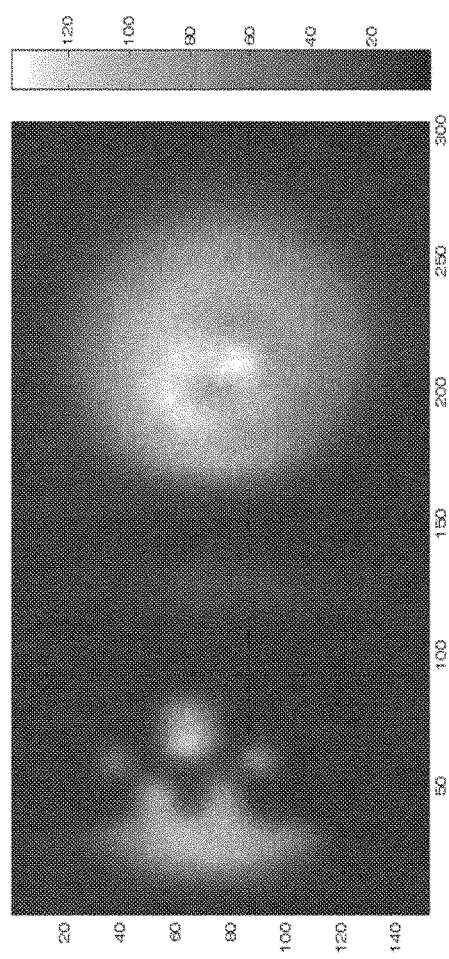
Figure 9B:
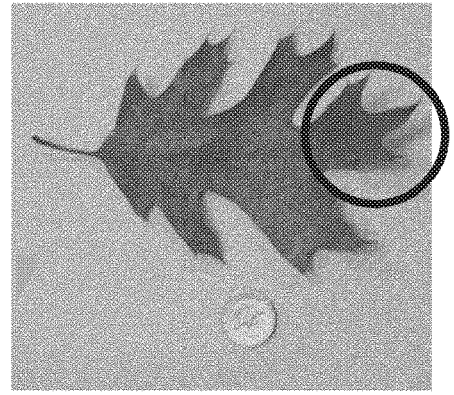
Figure 11B:
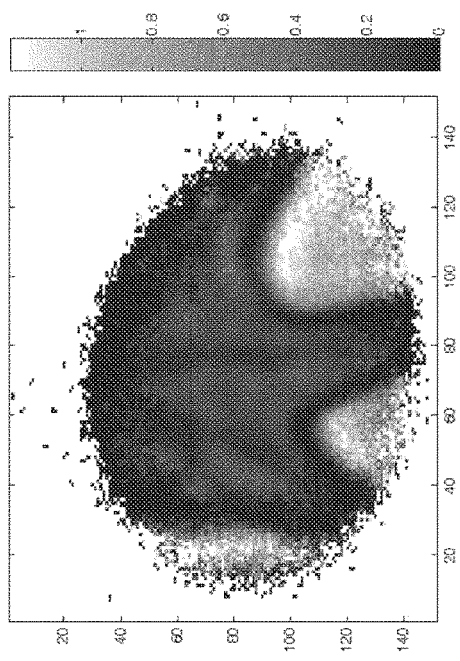
Figure 10B:
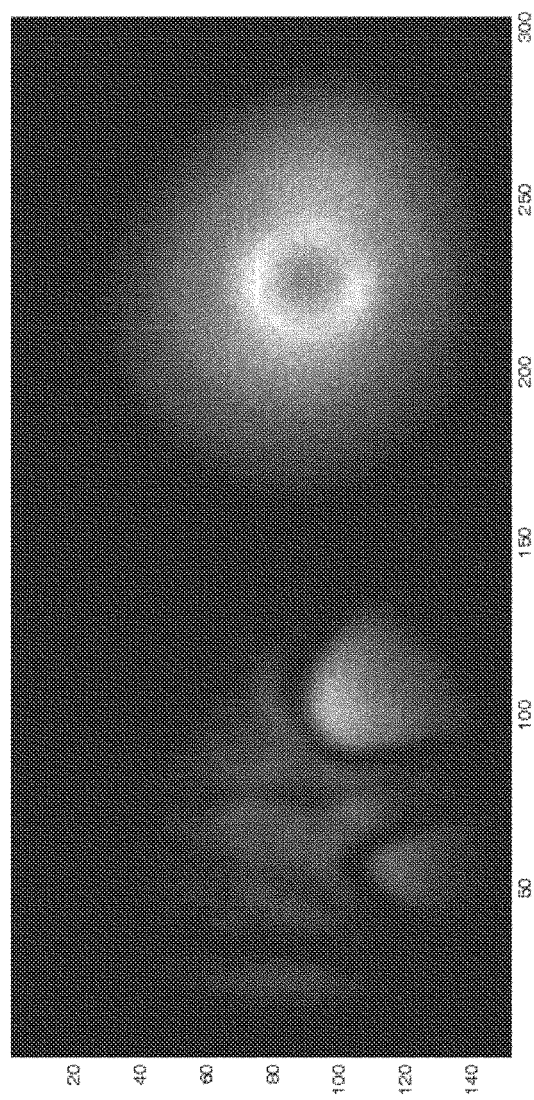
Figure 11C:
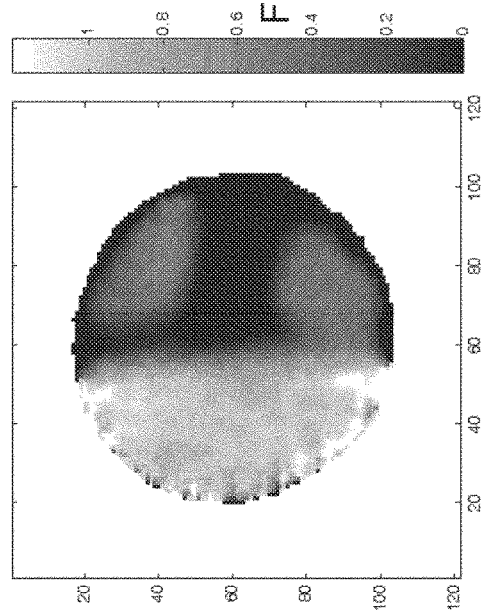
Figure 10C:
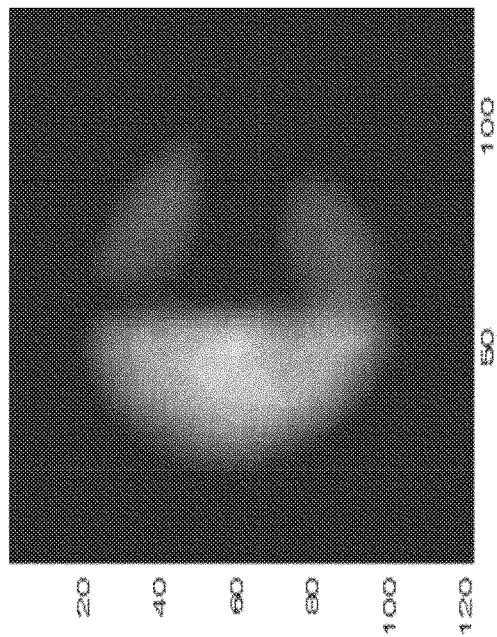
Figure 9C:
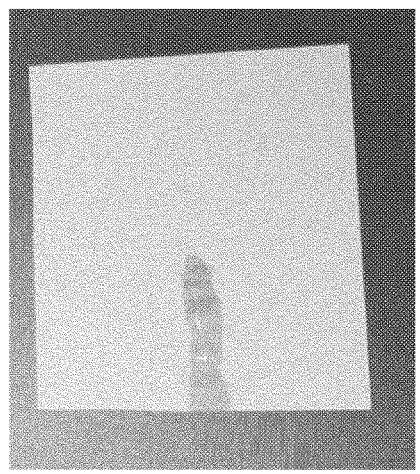

FIGS. 6A-6C show a cross-shaped aperture in a piece of sheet metal, a nut, and a razor blade, respectively, that were imaged (as object 10; in transmission) using upconversion of a terahertz image. FIGS. 7A-7C are the corresponding raw transmitted and upconverted images on the left and the upconverted terahertz imaging beam 21 (without the object 10) on the right, and FIGS. 8A-8C are the corresponding normalized, upconverted images (normalized by dividing the raw upconverted image beam by the upconverted terahertz imaging beam). FIGS. 9A-9C show a razor blade covered by adhesive tape, a leaf, and a piece of paper with water, respectively, that were imaged (as object 10; in transmission) using upconversion of a terahertz image. FIGS. 10A-10C are the corresponding raw transmitted and upconverted images and FIGS. 11A-11C are the corresponding normalized transmitted and upconverted images (normalized by dividing the raw upconverted image beam by the upconverted terahertz imaging beam). The examples of FIGS. 6A-8C demonstrate upconversion of transmitted terahertz images of objects that are opaque to terahertz radiation (i.e., upconversion of the terahertz "shadows" of such objects). The examples of FIGS. 9A-11C demonstrate upconversion of transmitted terahertz images of objects having spatially varying terahertz transmission (e.g., the veins in the leaf or the wet region of the paper) or that have features not discernable under optical illumination (e.g., the razor blade concealed by the tape).

Figure 12:
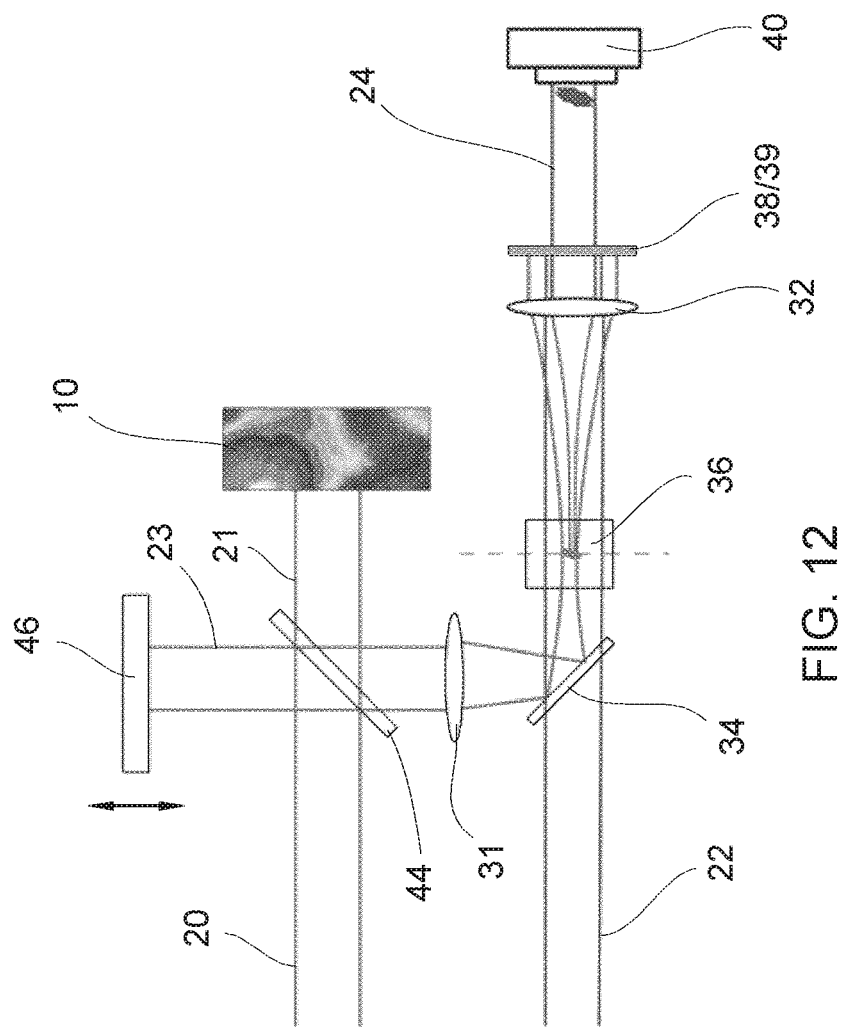
FIG. 12 illustrates schematically another example of an apparatus for acquiring an upconverted terahertz image using cw terahertz imaging beam and a cw upconverting beam.

Another example is illustrated schematically in FIG. 12 of a system for generating and acquiring reflected and upconverted terahertz images using so-called homodyne detection. In the preceding examples, the position dependent intensity of the upconverted terahertz image depends on only the intensity of the terahertz image, i.e., the position-dependent intensity of the upconverted image is substantially independent of position-dependent phase of that image. In this example a beam splitter 44 is employed to split off a terahertz reference beam 23 from the imaging terahertz beam 20. The beam splitter 44 combines the terahertz reference beam 23 with the terahertz image beam 21, which then co-propagate through the nonlinear optical medium 36. The relative phase of the terahertz reference beam 23 and the terahertz image beam 21 can be varied by varying the length of a delay line, e.g., as shown in FIG. 15. In this arrangement, the position-dependent intensity of each upconverted image depends at least partly on the corresponding relative phase of the terahertz image beam and the terahertz reference beam. Acquiring terahertz images that include both intensity and phase at each image position potentially can yield more information regarding the object 10 than image intensity alone. For example, a given object might yield a featureless image if only intensity is detected, but might exhibit image features manifested as phase variation across the image. Such an example is analogous to an object that is uniformly transparent to visible light but exhibits a spatially dependent index of refraction; an image consisting of only transmitted intensity would miss that spatial variation.

In the homodyne detection arrangement of FIG. 12, the combined terahertz reference beam 23 and terahertz image beam 21 arrive at the nonlinear optical medium 36 as a coherent superposition. The total terahertz intensity of the combined beams will include phase-independent portions that correspond to the squared amplitudes of the respective reference and image beams, and will also include a phase-dependent portion that corresponds to cross terms involving both amplitudes. In one example, the total intensity arises from upconversion of an image beam combined with a reference beam 100 times more intense than the image beam. Interference of those beams results in phase-dependent intensity variation of about ±20% of the reference intensity. This can be viewed as effectively amplifying the image beam, e.g., in some instances, depending on factors such as noise or detection sensitivity, a ±20% modulation of a non-zero background might be more readily detected and quantified than a nominally zero-background signal that is 100 times smaller.

Homodyne detection can be employed using a single detector: the detector is scanned across the upconverted image beam 24, and at each detector location the delay line is scanned to vary the relative phase of the terahertz reference and image beams. Alternatively, an array detector can be employed, acquiring a complete image at each different relative phase. In either case, the resulting images can be presented or interpreted according to standard methods for treating phase dependent quantities (e.g., using corresponding amplitude and phase images, or using so-called "in-phase" and "quadrature" images, which might also be referred to as real and imaginary parts of a complex-valued image). Homodyne detection techniques are widely employed in the field of optical coherence tomography; various numerical, computational, or analysis methods developed in that field can be readily applied to homodyne detection of upconverted terahertz images.

The configurations of FIG. 1, 2, or 5 can be modified to enable convenient acquisition of images of the object 10 at other wavelengths in addition to the upconverted terahertz images. For example, movable optics can be employed to redirect the upconverting beam 22 to propagate along the path of the terahertz imaging beam 21. The beamsplitter 34 and nonlinear optical medium 36 can be mounted so that they can be readily removed from the beam path, and the filter(s) 38 or polarizer 39 can be removed or replaced as appropriate. A filter wheel can be employed, for example, for swapping those elements into or out of the beam path. In this way, a given object can be imaged in place at differing wavelengths (e.g., 1.55 THz and 1064 nm) and then comparisons or correlations can be made among those images. In addition, other wavelengths (in addition to $\lambda_{UC}$) that might be available can be used for imaging object 10 as well.

In addition to the preceding, the following examples fall within the scope of the present disclosure or appended claims:

Example 1

A method for acquiring an upconverted terahertz image of an object, the method comprising: (a) illuminating the object with a continuous-wave terahertz imaging beam characterized by a terahertz frequency between about 0.05 THz and about 10 THz, a terahertz bandwidth, and a terahertz average power; (b) collecting at least a portion of the terahertz imaging beam, transmitted by or around the object or reflected or scattered from the object, and directing that portion to propagate as a terahertz image beam through a nonlinear optical medium, wherein the terahertz image beam is characterized by a terahertz image beam size at the nonlinear optical medium; (c) directing a continuous-wave upconverting beam to propagate through the nonlinear optical medium, wherein the upconverting beam at least partly spatially overlaps the terahertz image beam in the nonlinear optical medium and is characterized by an upconverting wavelength, an upconverting bandwidth, an upconverting average power, and an upconverting beam size at the nonlinear optical medium; (d) upconverting, by nonlinear optical interaction of the terahertz image beam and the upconverting beam in the nonlinear optical medium, at least a portion of the terahertz image beam to form an upconverted image beam characterized by one or both wavelengths produced by sum- or difference-frequency generation between the terahertz image beam and the upconverting beam; (e) receiving at least a portion of the upconverted image beam using an image detector and detecting with the image detector an upconverted image formed at the image detector by the upconverted image beam; and (f) allowing less than about 1 part in $10^6$ of the upconverting beam to reach the image detector using an image filtering element, (g) wherein the terahertz average power is greater than about 0.1 W, the upconverting wavelength is between about 400 nm and about 3500 nm, the upconverting bandwidth is less than about 0.1 nm, and the upconverting average power is greater than about 1 W.

Example 2

The method of Example 1 wherein the upconverting wavelength is between about 1000 nm and about 1100 nm, the upconverting bandwidth is less than about 0.01 nm, and the upconverting average power is greater than about 10 W.

Example 3

The method of Example 1 wherein the upconverting wavelength is between about 1500 nm and about 1600 nm, the upconverting bandwidth is less than about 0.01 nm, and the upconverting average power is greater than about 5 W.

Example 4

The method of any one of Examples 1 through 3 wherein a source of the upconverting beam is a solid state laser, a fiber laser, or a semiconductor laser.

Example 5

The method of any one of Examples 1 through 4 wherein: (i) the terahertz frequency is less than about 3 THz and the terahertz average power is greater than about 0.3 W, or (ii) the terahertz frequency is less than about 1.6 THz and the terahertz average power is greater than about 0.5 W.

Example 6

The method of any one of Examples 1 through 5 wherein a source of the terahertz beam includes a backward-wave-type oscillator, one or more terahertz amplifiers, or one or more harmonic generators.

Example 7

The method of any one of Examples 1 through 6 wherein the upconverted image wavelength is: (i) less than about 1 nm below or less than about 1 nm above the upconverting wavelength, or both, (ii) about 1 to 2 nm below or about 1 to 2 nm above the upconverting wavelength, or both, (iii) about 2 to 3 nm below or about 2 to 3 nm above the upconverting wavelength, or both, (iv) about 3 to 4 nm below or about 3 to 4 nm above the upconverting wavelength, or both, (v) about 4 to 5 nm below or about 4 to 5 nm above the upconverting wavelength, or both, or (vi) about 5 to 6 nm below or about 5 to 6 nm above the upconverting wavelength, or both.

Example 8

The method of any one of Examples 1 through 7 wherein the image filtering element is arranged to allow: (i) less than about 1 part in $10^6$ of the upconverting beam to reach the image detector; (ii) less than about 1 part in $10^7$ of the upconverting beam to reach the image detector; (iii) less than about 1 part in $10^8$ of the upconverting beam to reach the image detector; (iv) less than about 1 part in $10^{10}$ of the upconverting beam to reach the image detector; or (v) less than about 1 part in $10^{12}$ of the upconverting beam to reach the image detector.

Example 9

The method of any one of Examples 1 through 8 wherein the image filtering element includes one or more wavelength-dependent filters.

Example 10

The method of Example 9 wherein at least one of the one or more wavelength-dependent filters comprises a short-pass or a long-pass filter with a nominal cutoff wavelength between the upconverting wavelength and one of the upconverted image wavelengths.

Example 11

The method of any one of Examples 9 or 10 wherein at least one of the one or more wavelength-dependent filters comprises a notch filter nominally centered on the upconverting wavelength.

Example 12

The method of any one of Examples 1 through 11 wherein the nonlinear optical medium is arranged so that polarization of the upconverted image beam is substantially perpendicular to polarization of the upconverting beam.

Example 13

The method of any one of Examples 1 through 12 wherein the upconverting beam and the upconverted image beam are polarized substantially orthogonally with respect to each other, and the image filtering element includes one or more polarizers arranged to substantially block the upconverting beam.

Example 14

The method of any one of Examples 1 through 11 wherein the nonlinear optical medium is arranged so that polarization of the upconverted image beam is substantially parallel to polarization of the upconverting beam.

Example 15

The method of any one of Examples 1 through 14 wherein the nonlinear optical medium is arranged so that the nonlinear optical interaction is a critically phase-matched process.

Example 16

The method of any one of Examples 1 through 14 wherein the nonlinear optical medium is arranged so that the nonlinear optical interaction is a non-critically phase-matched process.

Example 17

The method of any one of Examples 1 through 14 wherein the nonlinear optical medium is arranged so that the nonlinear optical interaction is a quasi-phase-matched process.

Example 18

The method of Example 17 wherein the nonlinear optical medium comprises a periodically poled nonlinear optical crystal.

Example 19

The method of Example 17 wherein the nonlinear optical medium comprises a stack of two or more optically contacted plates of a nonlinear optical material.

Example 20

The method of Example 17 wherein the nonlinear optical medium comprises a stack of 6 to 12 optically contacted plates of GaAs about 300 μm thick, the terahertz frequency is about 1.55 THz, and the upconverting wavelength is about 1064 nm.

Example 21

The method of any one of Examples 1 through 16 wherein the nonlinear optical medium comprises a single GaAs plate up to about 8 to 9 mm thick, the terahertz frequency is about 0.3 THz, and the upconverting wavelength is about 1550 nm.

Example 22

The method of any one of Examples 1 through 21 wherein (i) a first focusing element collects the portion of the terahertz imaging beam and directs the terahertz image beam to propagate through the nonlinear optical medium, (ii) the object and the nonlinear optical medium are positioned at respective conjugate planes of the first focusing element so that the terahertz image beam forms a terahertz image of the object at the nonlinear optical medium, (iii) a second focusing element collects the portion of the upconverted image beam and directs the upconverted image beam to propagate to the image detector, and (iv) the nonlinear optical medium and the image detector are positioned at respective conjugate planes of the second focusing element so that the upconverted image beam forms the upconverted image at the image detector.

Example 23

The method of any one of Examples 1 through 21 wherein (i) a first focusing element, characterized by an effective focal length $f_1$, collects the portion of the terahertz imaging beam and directs the terahertz image beam to propagate through the nonlinear optical medium, (ii) the object and the nonlinear optical medium are each positioned at a distance of about $f_1$ from the first focusing element so that the terahertz image beam forms a spatial Fourier transform of a terahertz image of the object at the nonlinear optical medium, (iii) a second focusing element, characterized by an effective focal length $f_2$, collects the portion of the upconverted image beam and directs the upconverted image beam to propagate to the image detector, and (iv) the nonlinear optical medium and the image detector are each positioned at a distance of about $f_2$ from the second focusing element so that the upconverted image beam forms the upconverted image at the image detector.

Example 24

The method of any one of Examples 1 through 23 wherein the image detector comprises an imaging detector array, and detecting the upconverted image comprises receiving simultaneously different spatial portions of the upconverted image beam on multiple corresponding detector elements of the imaging detector array.

Example 25

The method of any one of Examples 1 through 23 wherein the image detector comprises a single detector element, and detecting the upconverted image comprises scanning the single detector element across the upconverted image beam so as to receive sequentially different spatial portions of the upconverted image beam on the single detector element.

Example 26

The method of any one of Examples 1 through 25 wherein position-dependent intensity of the upconverted image is substantially independent of position-dependent phase of the terahertz image.

Example 27

The method of any one of Examples 1 through 25 further comprising: splitting off a portion of the terahertz imaging beam to form a terahertz reference beam; combining the terahertz reference beam and the terahertz image beam to co-propagate through the nonlinear optical medium; and acquiring multiple upconverted terahertz images with corresponding different relative phases of the terahertz image beam and the terahertz reference beam, wherein position-dependent intensity of each upconverted image depends at least partly on the corresponding position-dependent relative phase of the terahertz image beam and the terahertz reference beam.

Example 28

An apparatus for acquiring an upconverted terahertz image of an object, the apparatus comprising: (a) a continuous-wave terahertz source arranged to illuminate the object with a terahertz imaging beam characterized by a terahertz frequency between about 0.05 THz and about 10 THz, a terahertz bandwidth, and a terahertz average power; (b) one or more terahertz optical components arranged to collect at least a portion of the terahertz imaging beam, transmitted by or around the object or reflected or scattered from the object, and to direct that portion to propagate as a terahertz image beam through a nonlinear optical medium, wherein the terahertz image beam is characterized by a terahertz image beam size at the nonlinear optical medium; (c) a light source arranged to emit a continuous-wave upconverting beam; (d) one or more optical components arranged to direct the upconverting beam to propagate through the nonlinear optical medium, wherein the upconverting beam at least partly spatially overlaps the terahertz image beam in the nonlinear optical medium and is characterized by an upconverting wavelength, an upconverting bandwidth, an upconverting average power, and an upconverting beam size at the nonlinear optical medium; (e) the nonlinear optical medium, wherein the nonlinear optical medium is arranged to upconvert, by nonlinear optical interaction of the terahertz image beam and the upconverting beam in the nonlinear optical medium, at least a portion of the terahertz image beam to form an upconverted image beam characterized by one or both wavelengths produced by sum- or difference-frequency generation between the terahertz image beam and the upconverting beam; (f) an image detector arranged to receive at least a portion of the upconverted image beam and to detect an upconverted image formed at the image detector by the upconverted image beam; and (g) an image filtering element arranged to allow less than about 1 part in $10^6$ of the upconverting beam to reach the image detector, (h) wherein the upconverting wavelength is between about 400 nm and about 3500 nm, the upconverting bandwidth is less than about 0.1 nm, and the upconverting average power is greater than about 1 W.

Example 29

The apparatus of Example 28 wherein the upconverting wavelength is between about 1000 nm and about 1100 nm, the upconverting bandwidth is less than about 0.01 nm, and the upconverting average power is greater than about 10 W.

Example 30

The apparatus of Example 28 the upconverting wavelength is between about 1500 nm and about 1600 nm, the upconverting bandwidth is less than about 0.01 nm, and the upconverting average power is greater than about 5 W.

Example 31

The apparatus of any one of Examples 28 through 30 wherein a source of the upconverting beam is a solid state laser, a fiber laser, or a semiconductor laser.

Example 32

The apparatus of any one of Examples 28 through 31 wherein: (i) the terahertz frequency is less than about 3 THz and the terahertz average power is greater than about 0.3 W, or (ii) the terahertz frequency is less than about 1.6 THz and the terahertz average power is greater than about 0.5 W.

Example 33

The apparatus of any one of Examples 28 through 32 wherein a source of the terahertz beam includes a backward-wave-type oscillator, one or more terahertz amplifiers, or one or more harmonic generators.

Example 34

The apparatus of any one of Examples 28 through 33 wherein the upconverted image wavelength is: (i) less than about 1 nm below or less than about 1 nm above the upconverting wavelength, or both, (ii) about 1 to 2 nm below or about 1 to 2 nm above the upconverting wavelength, or both, (iii) about 2 to 3 nm below or about 2 to 3 nm above the upconverting wavelength, or both, (iv) about 3 to 4 nm below or about 3 to 4 nm above the upconverting wavelength, or both, (v) about 4 to 5 nm below or about 4 to 5 nm above the upconverting wavelength, or both, or (vi) about 5 to 6 nm below or about 5 to 6 nm above the upconverting wavelength, or both.

Example 35

The apparatus of any one of Examples 28 through 34 wherein the image filtering element is arranged to allow: (i) less than about 1 part in $10^6$ of the upconverting beam to reach the image detector; (ii) less than about 1 part in $10^7$ of the upconverting beam to reach the image detector; (iii) less than about 1 part in $10^8$ of the upconverting beam to reach the image detector; (iv) less than about 1 part in $10^{10}$ of the upconverting beam to reach the image detector; or (v) less than about 1 part in $10^{12}$ of the upconverting beam to reach the image detector.

Example 36

The apparatus of any one of Examples 28 through 35 wherein the image filtering element includes one or more wavelength-dependent filters.

Example 37

The apparatus of Example 36 wherein at least one of the one or more wavelength-dependent filters comprises a short-pass or a long-pass filter with a nominal cutoff wavelength between the upconverting wavelength and one of the upconverted image wavelengths.

Example 38

The apparatus of any one of Examples 36 or 37 wherein at least one of the one or more wavelength-dependent filters comprises a notch filter nominally centered on the upconverting wavelength.

Example 39

The apparatus of any one of Examples 28 through 38 wherein the nonlinear optical medium is arranged so that polarization of the upconverted image beam is substantially perpendicular to polarization of the upconverting beam.

Example 40

The apparatus of any one of Examples 28 through 39 wherein the upconverting beam and the upconverted image beam are polarized substantially orthogonally with respect to each other, and the image filtering element includes one or more polarizers arranged to substantially block the upconverting beam.

Example 41

The apparatus of any one of Examples 28 through 38 wherein the nonlinear optical medium is arranged so that polarization of the upconverted image beam is substantially parallel to polarization of the upconverting beam.

Example 42

The apparatus of any one of Examples 28 through 41 wherein the nonlinear optical medium is arranged so that the nonlinear optical interaction is a critically phase-matched process.

Example 43

The apparatus of any one of Examples 28 through 41 wherein the nonlinear optical medium is arranged so that the nonlinear optical interaction is a non-critically phase-matched process.

Example 44

The apparatus of any one of Examples 29 through 41 wherein the nonlinear optical medium is arranged so that the nonlinear optical interaction is a quasi-phase-matched process.

Example 45

The apparatus of Example 44 wherein the nonlinear optical medium comprises a periodically poled nonlinear optical crystal.

Example 46

The apparatus of Example 44 wherein the nonlinear optical medium comprises a stack of two or more optically contacted plates of a nonlinear optical material.

Example 47

The apparatus of Example 44 wherein the nonlinear optical medium comprises a stack of 6 to 12 optically contacted plates of GaAs about 300 μm thick, the terahertz frequency is about 1.55 THz, and the upconverting wavelength is about 1064 nm.

Example 48

The apparatus of any one of Examples 28 through 43 wherein the nonlinear optical medium comprises a GaAs plate up to about 8 to 9 mm thick, the terahertz frequency is about 0.3 THz, and the upconverting wavelength is about 1550 nm.

Example 49

The apparatus of any one of Examples 28 through 48 wherein (i) the one or more terahertz optical components include a first focusing element arranged to collect the portion of the terahertz imaging beam and to direct the terahertz image beam to propagate through the nonlinear optical medium, (ii) the object and the nonlinear optical medium are positioned at respective conjugate planes of the first focusing element so that the terahertz image beam forms a terahertz image of the object at the nonlinear optical medium, (iii) the one or more optical components include a second focusing element arranged to collect the portion of the upconverted image beam and to direct the upconverted image beam to propagate to the image detector, and (iv) the nonlinear optical medium and the image detector are positioned at respective conjugate planes of the second focusing element so that the upconverted image beam forms the upconverted image at the image detector.

Example 50

The apparatus of any one of Examples 28 through 48 wherein (i) the one or more terahertz optical components include a first focusing element, characterized by an effective focal length $f_1$, arranged to collect the portion of the terahertz imaging beam and to direct the terahertz image beam to propagate through the nonlinear optical medium, (ii) the object and the nonlinear optical medium are each positioned at a distance of about $f_1$ from the first focusing element so that the terahertz image beam forms a spatial Fourier transform of a terahertz image of the object at the nonlinear optical medium, (iii) the one or more optical components include a second focusing element, characterized by an effective focal length $f_2$, arranged to collect the portion of the upconverted image beam and to direct the upconverted image beam to propagate to the image detector, and (iv) the nonlinear optical medium and the image detector are each positioned at a distance of about $f_2$ from the second focusing element so that the upconverted image beam forms the upconverted image at the image detector.

Example 51

The apparatus of any one of Examples 28 through 50 wherein the image detector comprises an imaging detector array positioned and arranged to receive simultaneously different spatial portions of the upconverted image beam on multiple corresponding detector elements of the imaging detector array.

Example 52

The apparatus of any one of Examples 28 through 50 wherein the image detector comprises a single detector element arranged to be scanned across the upconverted image beam so as to receive sequentially different spatial portions of the upconverted image beam on the single detector element.

Example 53

The apparatus of any one of Examples 28 through 52 wherein one or both of the one or more terahertz optical components or the one or more optical components are arranged so that position-dependent intensity of the upconverted image is substantially independent of position-dependent phase of the terahertz image.

Example 54

The apparatus of any one of Examples 28 through 52 wherein the one or more terahertz optical components are arranged to split off a portion of the terahertz imaging beam to form a terahertz reference beam and to combine the terahertz reference beam and the terahertz image beam to co-propagate through the nonlinear optical medium with different relative phase of the terahertz image beam and the terahertz reference beam, and position-dependent intensity of each upconverted image depends at least partly on the corresponding relative phase of the terahertz image beam and the terahertz reference beam.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., a set of features that are neither incompatible nor mutually exclusive) that appear in the present disclosure or the appended claims, including those sets that may not be explicitly disclosed herein. In addition, for purposes of disclosure, each of the appended dependent claims shall be construed as if written in multiple dependent form and dependent upon all preceding claims with which it is not inconsistent. It should be further noted that the scope of the appended claims does not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open ended terminology, with the same meaning as if the phrase "at least" were appended after each instance thereof, unless explicitly stated otherwise. For purposes of the present disclosure or appended claims, when terms are employed such as "about equal to," "substantially equal to," "greater than about," "less than about," and so forth, in relation to a numerical quantity, standard conventions pertaining to measurement precision and significant digits shall apply, unless a differing interpretation is explicitly set forth. For null quantities described by phrases such as "substantially prevented," "substantially absent," "substantially eliminated," "about equal to zero," "negligible," and so forth, each such phrase shall denote the case wherein the quantity in question has been reduced or diminished to such an extent that, for practical purposes in the context of the intended operation or use of the disclosed or claimed apparatus or method, the overall behavior or performance of the apparatus or method does not differ from that which would have occurred had the null quantity in fact been completely removed, exactly equal to zero, or otherwise exactly nulled.

In the appended claims, any labelling of elements, steps, limitations, or other portions of a claim (e.g., first, second, etc., (a), (b), (c), etc., or (i), (ii), (iii), etc.) is only for purposes of clarity, and shall not be construed as implying any sort of ordering or precedence of the claim portions so labelled. If any such ordering or precedence is intended, it will be explicitly recited in the claim or, in some instances, it will be implicit or inherent based on the specific content of the claim. In the appended claims, if the provisions of 35 USC §112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC §112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. A method for acquiring an upconverted terahertz image of an object, the method comprising:
    (a) illuminating the object with a continuous-wave terahertz imaging beam characterized by a terahertz frequency between about 0.05 THz and about 10 THz, a terahertz bandwidth, and a terahertz average power;
    (b) collecting at least a portion of the terahertz imaging beam, transmitted by or around the object or reflected or scattered from the object, and directing that portion to propagate as a terahertz image beam through a nonlinear optical medium, wherein the terahertz image beam is characterized by a terahertz image beam size at the nonlinear optical medium;
    (c) directing a continuous-wave upconverting beam to propagate through the nonlinear optical medium, wherein the upconverting beam at least partly spatially overlaps the terahertz image beam in the nonlinear optical medium and is characterized by an upconverting wavelength, an upconverting bandwidth, an upconverting average power, and an upconverting beam size at the nonlinear optical medium;
    (d) upconverting, by nonlinear optical interaction of the terahertz image beam and the upconverting beam in the nonlinear optical medium, at least a portion of the terahertz image beam to form an upconverted image beam characterized by one or both wavelengths produced by sum- or difference-frequency generation between the terahertz image beam and the upconverting beam;
    (e) receiving at least a portion of the upconverted image beam using an image detector and detecting with the image detector an upconverted image formed at the image detector by the upconverted image beam; and
    (f) allowing less than about 1 part in $10^6$ of the upconverting beam to reach the image detector using an image filtering element,
    (g) wherein the terahertz average power is greater than about 0.1 W, the upconverting wavelength is between about 400 nm and about 3500 nm, the upconverting bandwidth is less than about 0.1 nm, and the upconverting average power is greater than about 1 W.

2. The method of claim 1 wherein the upconverting wavelength is between about 1000 nm and about 1100 nm, the upconverting bandwidth is less than about 0.01 nm, and the upconverting average power is greater than about 10 W.

3. The method of claim 1 wherein the upconverting wavelength is between about 1500 nm and about 1600 nm, the upconverting bandwidth is less than about 0.01 nm, and the upconverting average power is greater than about 5 W.

4. The method of claim 1 wherein a source of the upconverting beam is a solid state laser, a fiber laser, or a semiconductor laser.

5. The method of claim 1 wherein the terahertz frequency is less than about 3 THz and the terahertz average power is greater than about 0.3 W.

6. The method of claim 1 wherein the terahertz frequency is less than about 1.6 THz and the terahertz average power is greater than about 0.5 W.

7. The method of claim 1 wherein a source of the terahertz beam includes a backward-wave-type oscillator, one or more terahertz amplifiers, or one or more harmonic generators.

8. The method of claim 1 wherein the image filtering element includes one or more wavelength-dependent filters.

9. The method of claim 8 wherein at least one of the one or more wavelength-dependent filters comprises a short-pass or a long-pass filter with a nominal cutoff wavelength between the upconverting wavelength and one of the upconverted image wavelengths.

10. The method of claim 8 wherein at least one of the one or more wavelength-dependent filters comprises a notch filter with a rejection bandwidth that includes the upconverting wavelength.

11. The method of claim 1 wherein the upconverting beam and the upconverted image beam are polarized substantially orthogonally with respect to each other, and the image filtering element includes one or more polarizers arranged to substantially block the upconverting beam.

12. The method of claim 1 wherein the nonlinear optical medium is arranged so that the nonlinear optical interaction is a quasi-phase-matched process.

13. The method of claim 12 wherein the nonlinear optical medium comprises a stack of two or more optically contacted plates of a nonlinear optical material.

14. The method of claim 1 wherein (i) a first focusing element collects the portion of the terahertz imaging beam and directs the terahertz image beam to propagate through the nonlinear optical medium, (ii) the object and the nonlinear optical medium are positioned at respective conjugate planes of the first focusing element so that the terahertz image beam forms a terahertz image of the object at the nonlinear optical medium, (iii) a second focusing element collects the portion of the upconverted image beam and directs the upconverted image beam to propagate to the image detector, and (iv) the nonlinear optical medium and the image detector are positioned at respective conjugate planes of the second focusing element so that the upconverted image beam forms the upconverted image at the image detector.

15. The method of claim 1 wherein (i) a first focusing element, characterized by an effective focal length $f_1$, collects the portion of the terahertz imaging beam and directs the terahertz image beam to propagate through the nonlinear optical medium, (ii) the object and the nonlinear optical medium are each positioned at a distance of about $f_1$ from the first focusing element so that the terahertz image beam forms a spatial Fourier transform of a terahertz image of the object at the nonlinear optical medium, (iii) a second focusing element, characterized by an effective focal length $f_2$, collects the portion of the upconverted image beam and directs the upconverted image beam to propagate to the image detector, and (iv) the nonlinear optical medium and the image detector are each positioned at a distance of about $f_2$ from the second focusing element so that the upconverted image beam forms the upconverted image at the image detector.

16. The method of claim 1 wherein the image detector comprises an imaging detector array, and detecting the upconverted image comprises receiving simultaneously different spatial portions of the upconverted image beam on multiple corresponding detector elements of the imaging detector array.

17. The method of claim 1 further comprising: splitting off a portion of the terahertz imaging beam to form a terahertz reference beam; combining the terahertz reference beam and the terahertz image beam to co-propagate through the nonlinear optical medium; and acquiring multiple upconverted terahertz images with corresponding different relative phases of the terahertz image beam and the terahertz reference beam, wherein position-dependent intensity of each upconverted image depends at least partly on the corresponding position-dependent relative phase of the terahertz image beam and the terahertz reference beam.

18. An apparatus for acquiring an upconverted terahertz image of an object, the apparatus comprising:
(a) a terahertz source arranged to illuminate the object with a continuous-wave terahertz imaging beam characterized by a terahertz frequency between about 0.05 THz and about 10 THz, a terahertz bandwidth, and a terahertz average power;
(b) one or more terahertz optical components arranged to collect at least a portion of the terahertz imaging beam, transmitted by or around the object or reflected or scattered from the object, and to direct that portion to propagate as a terahertz image beam through a nonlinear optical medium, wherein the terahertz image beam is characterized by a terahertz image beam size at the nonlinear optical medium;
(c) a light source arranged to emit a continuous-wave upconverting beam;
(d) one or more optical components arranged to direct the upconverting beam to propagate through the nonlinear optical medium, wherein the upconverting beam at least partly spatially overlaps the terahertz image beam in the nonlinear optical medium and is characterized by an upconverting wavelength, an upconverting bandwidth, an upconverting average power, and an upconverting beam size at the nonlinear optical medium;
(e) the nonlinear optical medium, wherein the nonlinear optical medium is arranged to upconvert, by nonlinear optical interaction of the terahertz image beam and the upconverting beam in the nonlinear optical medium, at least a portion of the terahertz image beam to form an upconverted image beam characterized by one or both wavelengths produced by sum- or difference-frequency generation between the terahertz image beam and the upconverting beam;
(f) an image detector arranged to receive at least a portion of the upconverted image beam and to detect an upconverted image formed at the image detector by the upconverted image beam; and
(g) an image filtering element arranged to allow less than about 1 part in $10^6$ of the upconverting beam to reach the image detector,
(h) wherein the upconverting wavelength is between about 400 nm and about 3500 nm, the upconverting bandwidth is less than about 0.1 nm, and the upconverting average power is greater than about 1 W.

19. The apparatus of claim 18 wherein the upconverting wavelength is between about 1000 nm and about 1100 nm, the upconverting bandwidth is less than about 0.01 nm, and the upconverting average power is greater than about 10 W.

20. The apparatus of claim 18 wherein the upconverting wavelength is between about 1500 nm and about 1600 nm, the upconverting bandwidth is less than about 0.01 nm, and the upconverting average power is greater than about 5 W.

21. The apparatus of claim 18 wherein a source of the upconverting beam is a solid state laser, a fiber laser, or a semiconductor laser.

22. The apparatus of claim 18 wherein the terahertz frequency is less than about 3 THz and the terahertz average power is greater than about 0.3 W.

23. The apparatus of claim 18 wherein the terahertz frequency is less than about 1.6 THz and the terahertz average power is greater than about 0.5 W.

24. The apparatus of claim 18 wherein a source of the terahertz beam includes a backward-wave-type oscillator, one or more terahertz amplifiers, or one or more harmonic generators.

25. The apparatus of claim 18 wherein the image filtering element includes one or more wavelength-dependent filters.

26. The apparatus of claim 25 wherein at least one of the one or more wavelength-dependent filters comprises a short-pass or a long-pass filter with a nominal cutoff wavelength between the upconverting wavelength and one of the upconverted image wavelengths.

27. The apparatus of claim 25 wherein at least one of the one or more wavelength-dependent filters comprises a notch filter with a rejection bandwidth that includes the upconverting wavelength.

28. The apparatus of claim 18 wherein the upconverting beam and the upconverted image beam are polarized substantially orthogonally with respect to each other, and the image filtering element includes one or more polarizers arranged to substantially block the upconverting beam.

29. The apparatus of claim 18 wherein the nonlinear optical medium is arranged so that the nonlinear optical interaction is a quasi-phase-matched process.

30. The apparatus of claim 29 wherein the nonlinear optical medium comprises a stack of two or more optically contacted plates of a nonlinear optical material.

31. The apparatus of claim 18 wherein (i) the one or more terahertz optical components include a first focusing element arranged to collect the portion of the terahertz imaging beam and to direct the terahertz image beam to propagate through the nonlinear optical medium, (ii) the object and the nonlinear optical medium are positioned at respective conjugate planes of the first focusing element so that the terahertz image beam forms a terahertz image of the object at the nonlinear optical medium, (iii) the one or more optical components include a second focusing element arranged to collect the portion of the upconverted image beam and to direct the upconverted image beam to propagate to the image detector, and (iv) the nonlinear optical medium and the image detector are positioned at respective conjugate planes of the second focusing element so that the upconverted image beam forms the upconverted image at the image detector.

32. The apparatus of claim 18 wherein (i) the one or more terahertz optical components include a first focusing element, characterized by an effective focal length $f_1$, arranged to collect the portion of the terahertz imaging beam and to direct the terahertz image beam to propagate through the nonlinear optical medium, (ii) the object and the nonlinear optical medium are each positioned at a distance of about $f_1$ from the first focusing element so that the terahertz image beam forms a spatial Fourier transform of a terahertz image of the object at the nonlinear optical medium, (iii) the one or more optical components include a second focusing element, characterized by an effective focal length $f_2$, arranged to collect the portion of the upconverted image beam and to direct the upconverted image beam to propagate to the image detector, and (iv) the nonlinear optical medium and the image detector are each positioned at a distance of about $f_2$ from the second focusing element so that the upconverted image beam forms the upconverted image at the image detector.

33. The apparatus of claim 18 wherein the image detector comprises an imaging detector array positioned and arranged to receive simultaneously different spatial portions of the upconverted image beam on multiple corresponding detector elements of the imaging detector array.

34. The apparatus of claim 18 wherein the one or more terahertz optical components are arranged to split off a portion of the terahertz imaging beam to form a terahertz reference beam and to combine the terahertz reference beam and the terahertz image beam to co-propagate through the nonlinear optical medium with different relative phase of the terahertz image beam and the terahertz reference beam, and position-dependent intensity of each upconverted image depends at least partly on the corresponding position-dependent relative phase of the terahertz image beam and the terahertz reference beam.

* * * * *